(12) United States Patent
Ogawa et al.

(10) Patent No.: US 11,007,678 B2
(45) Date of Patent: May 18, 2021

(54) PRODUCTION METHOD OF MOLD, MANUFACTURING METHOD OF PATTERN SHEET, PRODUCTION METHOD OF ELECTROFORM, AND PRODUCTION METHOD OF MOLD USING ELECTROFORM

(71) Applicant: FUJIFILM Corporation, Tokyo (JP)

(72) Inventors: Shotaro Ogawa, Ashigarakami-gun (JP); Satoshi Chai, Ashigarakami-gun (JP); Kenji Ichikawa, Ashigarakami-gun (JP); Kazunori Komatsu, Ashigarakami-gun (JP); Kozue Ikeda, Ashigarakami-gun (JP); Ryo Hibino, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 407 days.

(21) Appl. No.: 15/933,573

(22) Filed: Mar. 23, 2018

(65) Prior Publication Data
US 2018/0215078 A1     Aug. 2, 2018

Related U.S. Application Data

(63) Continuation of application No. PCT/JP2016/076340, filed on Sep. 7, 2016.

(30) Foreign Application Priority Data

Sep. 30, 2015 (JP) .............................. JP2015-193480
May 16, 2016 (JP) .............................. JP2016-097825

(51) Int. Cl.
*B29C 33/38* (2006.01)
*B29C 33/42* (2006.01)
(Continued)

(52) U.S. Cl.
CPC ......... *B29C 33/3857* (2013.01); *A61M 37/00* (2013.01); *A61M 37/0015* (2013.01);
(Continued)

(58) Field of Classification Search
CPC .............. A61M 37/00; A61M 37/0015; A61M 2037/46; A61M 2037/53; B29C 33/3857;
(Continued)

(56) References Cited

U.S. PATENT DOCUMENTS

2005/0082700 A1* 4/2005 Deeman .................. C25D 1/20
264/2.5
2006/0279025 A1 12/2006 Heidari et al.
(Continued)

FOREIGN PATENT DOCUMENTS

JP        H10-44255 A      2/1998
JP        2007-535343 A    12/2007
(Continued)

OTHER PUBLICATIONS

Communication dated Oct. 31, 2019 from the Korean Intellectual Property Office in counterpart KR Application No. 10-2018-7006454.
(Continued)

*Primary Examiner* — Matthew J Daniels
*Assistant Examiner* — Gregory Chad Grosso
(74) *Attorney, Agent, or Firm* — Sughrue Mion, PLLC

(57) ABSTRACT

A production method of a mold includes: preparing a plate precursor having a protruding pattern formed of protrusions in a pattern presence region on a base, and a thermoplastic resin sheet; determining a position at which the plate precursor is to be pressed against the thermoplastic resin sheet by moving the plate precursor and the thermoplastic resin sheet relative to each other; and forming a recessed pattern on the thermoplastic resin sheet by pressing the protrusions
(Continued)

of the plate precursor which is heated against the thermoplastic resin sheet at a position where a part of the pattern presence region of the plate precursor excluding the protrusions is separated from a surface of the thermoplastic resin sheet, cooling the plate precursor in a state in where the pressed protrusions and the thermoplastic resin sheet are in contact with each other, and separating the plate precursor from the thermoplastic resin sheet.

12 Claims, 20 Drawing Sheets

(51) Int. Cl.
*B81C 99/00* (2010.01)
*A61M 37/00* (2006.01)
*B29C 43/52* (2006.01)
*B29C 33/40* (2006.01)
*B29C 41/20* (2006.01)
*B29C 41/38* (2006.01)
*B29C 41/42* (2006.01)
*C25D 1/10* (2006.01)
*B29K 101/12* (2006.01)
*B29L 7/00* (2006.01)
*B29L 31/00* (2006.01)

(52) U.S. Cl.
CPC ............... *B29C 33/40* (2013.01); *B29C 33/42* (2013.01); *B29C 41/20* (2013.01); *B29C 41/38* (2013.01); *B29C 41/42* (2013.01); *B29C 43/52* (2013.01); *B81C 99/00* (2013.01); *C25D 1/10* (2013.01); *A61M 2037/0046* (2013.01); *A61M 2037/0053* (2013.01); *B29K 2101/12* (2013.01); *B29L 2007/00* (2013.01); *B29L 2031/759* (2013.01)

(58) Field of Classification Search
CPC ......... B29C 33/40; B29C 33/42; B29C 33/52; B29C 41/20; B29C 41/38; B29C 41/42; B81C 99/00; C25D 1/10; B29K 2101/12; B29L 2007/00; B29L 2031/759

USPC ........................................................ 264/138
See application file for complete search history.

(56) References Cited

U.S. PATENT DOCUMENTS

| 2007/0172967 A1* | 7/2007 | Katagiri ................. B82Y 10/00 438/14 |
| 2008/0221532 A1* | 9/2008 | Ogawa .............. A61M 37/0015 604/272 |
| 2009/0318833 A1 | 12/2009 | Lim |
| 2010/0305516 A1 | 12/2010 | Xu et al. |
| 2011/0127690 A1 | 6/2011 | Honda et al. |
| 2011/0192562 A1 | 8/2011 | Motoi et al. |
| 2015/0238743 A1 | 8/2015 | Che et al. |

FOREIGN PATENT DOCUMENTS

| JP | 2008-044283 A | 2/2008 |
| JP | 2010-503454 A | 2/2010 |
| JP | 2011-078617 A | 4/2011 |
| JP | 2011-078618 A | 4/2011 |
| JP | 2011-083993 A | 4/2011 |
| JP | 2012-055343 A | 3/2012 |

OTHER PUBLICATIONS

Communication dated Apr. 19, 2019, from Korean Intellectual Property Office in counterpart application No. 10-2018-7006454.
Communication dated Feb. 4, 2019, from European Patent Office in counterpart application No. 16851068.3.
International Search Report for PCT/JP2016/076340 dated Oct. 11, 2016 [PCT/ISA/210].
Written Opinion of the International Searching Authority dated Oct. 11, 2016, in counterpart International Application No. PCT/JP2016/076340.
International Preliminary Report on Patentability dated Apr. 18, 2018, in counterpart International Application No. PCT/JP2016/076340.

* cited by examiner

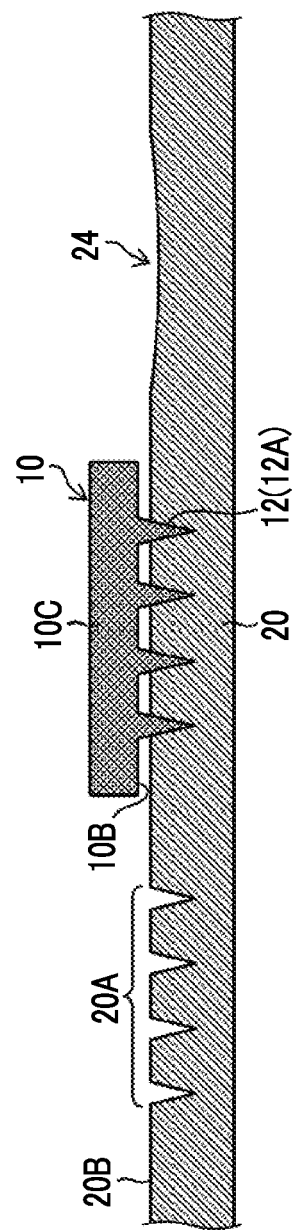

PRODUCTION METHOD OF MOLD, MANUFACTURING METHOD OF PATTERN SHEET, PRODUCTION METHOD OF ELECTROFORM, AND PRODUCTION METHOD OF MOLD USING ELECTROFORM

CROSS-REFERENCE TO RELATED APPLICATIONS

This application is a Continuation of PCT International Application No. PCT/JP2016/076340 filed on Sep. 7, 2016, which claims priorities under 35 U.S.C. § 119(a) to Japanese Patent Application No. 2015-193480 filed on Sep. 30, 2015 and Japanese Patent Application No. 2016-097825 filed on May 16, 2016. Each of the above applications is hereby expressly incorporated by reference, in their entirety, into the present application.

BACKGROUND OF THE INVENTION

1. Field of the Invention

The present invention relates to a production method of a mold, a manufacturing method of a pattern sheet, a production method of an electroform, and a production method of a mold using an electroform.

2. Description of the Related Art

In recent years, as a novel dosage form capable of injecting drugs such as insulin, vaccines, and human growth hormone (hGH) into the skin without pain, a microneedle array has been known. The microneedle array is an array of microneedles (also referred to as fine needles or small needles) which contain drugs and are biodegradable. By attaching this microneedle array to the skin, each microneedle pierces the skin, these microneedles are absorbed in the skin such that the drugs contained in each microneedle can be administered into the skin. Microneedle arrays are also called percutaneous absorption sheets.

In order to produce a formed product having a fine protruding pattern like the microneedle array as described above, a resin mold having the inverted shape is formed from a plate precursor having a fine protruding pattern, and a formed product is produced from the mold. There is a demand for improving the productivity of formed products having fine patterns, and various proposals have been made.

JP2007-535343A discloses a production method of a mold base for manufacturing microneedles. In the technique described in JP2007-535343 A, a mold base for manufacturing microneedles is produced by pressing a master model having master model needle arrays against a mold plate for manufacturing microneedles, and a formed product having a fine pattern is produced by using the mold base for manufacturing microneedles.

JP2011-083993A discloses transferring a transfer pattern formed on a mold to a plurality of points of a thermoplastic resin. In the technique described in JP2011-083993A, a heated mold is pressed against a thermoplastic resin and is cooled, and the mold is separated from the thermoplastic resin, thereby transferring the transfer pattern of the mold to the thermoplastic resin. Furthermore, moving the heated mold, pressing the mold against the thermoplastic resin and cooling the mold, and separating the mold from the thermoplastic resin are repeated, thereby transferring the transfer pattern of the mold to the thermoplastic resin.

SUMMARY OF THE INVENTION

In the technique described in JP2007-535343A, the master model (plate precursor) having a plurality of the master model needle arrays (for example, 8×8) is used. That is, a large master model is required, and thus there is concern that the number of operations for producing the master model may increase.

In the technique described in JP2011-083993A, the transfer pattern of the mold is transferred to the thermoplastic resin while pressing the flat surface of the mold against the thermoplastic resin. Therefore, there may be cases where the thermoplastic resin is raised at the end portion of the mold, and as a result, there is concern that a step may be formed between the molds. In a case where a duplicate mold (also called an electroform) is formed by electroforming or a formed product such as a percutaneous absorption sheet is manufactured, there may be cases where the step adversely affects the precision and productivity of the duplicate mold or the formed product.

FIG. 23A illustrates a step 2 formed at an end portion of a recess pattern of the surface of a produced mold 1, and FIG. 23B is an enlarged view of the step 2 in which a part in the circle of FIG. 23A is enlarged. As illustrated in FIG. 24, in a case where a duplicate mold 3 (or formed product) is manufactured by using the mold 1 having the step 2 at the end portion of the recess pattern of the mold 1, when the mold 1 is peeled away from the duplicate mold 3 (or formed product), peeling failure such as a difficulty in the peeling due to the step 2 acting as a resistance or breaking of the duplicate mold 3 (or formed product) at the step 2 is likely to occur.

The present invention has been made taking the above circumstances into consideration, and an object thereof is to provide a production method of a mold, a manufacturing method of a pattern sheet, a production method of an electroform, and a production method of a mold using an electroform, capable of suppressing the generation of a step at an end portion of a recessed pattern.

According to an aspect of the present invention, there is provided a production method of a mold comprising: a preparation process of preparing a plate precursor having a protruding pattern formed of a plurality of protrusions in a pattern presence region on a base, and a thermoplastic resin sheet; an alignment process of determining a position at which the plate precursor is to be pressed against the thermoplastic resin sheet by moving the plate precursor and the thermoplastic resin sheet relative to each other; and a forming process of forming a recessed pattern having an inverted shape of the protruding pattern on the thermoplastic resin sheet by pressing the protrusions of the plate precursor which is heated against the thermoplastic resin sheet at a position where a part of the pattern presence region of the plate precursor excluding the protrusions is separated from a surface of the thermoplastic resin sheet, cooling the plate precursor in a state in which the pressed protrusions and the thermoplastic resin sheet are in contact with each other, and separating the plate precursor from the thermoplastic resin sheet.

Preferably, a depression is formed in advance in a pressing surface in the surface of the thermoplastic resin sheet, against which the protrusions forming the protruding pattern of the plate precursor are pressed.

In the present invention, as described above, alternatively to the aspect in which the depression is formed in advance in the pressing surface in the surface of the thermoplastic resin sheet, against which the protruding pattern of the plate precursor is pressed, an aspect in which the pressing surface is flat may also be employed.

Preferably, in the forming process, in a case where a heating temperature of the plate precursor is equal to or lower than a melting point of the thermoplastic resin sheet, a vertical sectional shape of the depression is an arcuate shape.

Preferably, in the forming process, in a case where a heating temperature of the plate precursor is equal to or higher than a melting point of the thermoplastic resin sheet, a vertical sectional shape of the depression is a rectangular shape.

Here, the depression having an arcuate vertical sectional shape refers to a depression having a side surface which is curved with respect to the bottom surface of the depression. In addition, the depression having a rectangular vertical sectional shape refers to a depression having a side surface at a right angle to the bottom surface of the depression.

Preferably, the pressing surface in the surface of the thermoplastic resin sheet, against which the protrusions forming the protruding pattern of the plate precursor are pressed, is flat, and in the forming process, the part of the pattern presence region of the plate precursor excluding the protrusions is stopped before reaching the flat pressing surface.

Preferably, in a case where the plate precursor is pressed against the thermoplastic resin sheet, a position of the surface of the thermoplastic resin sheet is detected, and the plate precursor is pushed from the position of the surface of the thermoplastic resin sheet by a certain amount.

Preferably, in a case where the plate precursor is pressed against the thermoplastic resin sheet, a pressure applied to the plate precursor is measured and is compared to a certain pressure value which is set, and the amount of the plate precursor being pushed is determined.

Preferably, the protrusion forming the protruding pattern has a frustum portion and a needle portion which is tapered, in a direction away from the base of the plate precursor, and in the forming process, in a case where the plate precursor is pressed against the thermoplastic resin sheet, the frustum portion is brought into contact with the surface of the thermoplastic resin sheet.

According to another aspect of the present invention, there is provided a manufacturing method of a pattern sheet having a protruding pattern, comprising: a process of producing a mold using the production method described above; a supplying process of supplying a polymer solution to a recessed pattern of the mold; a drying process of drying the polymer solution to form a polymer sheet; and a polymer sheet peeling process of peeling the polymer sheet from the mold.

According to another aspect of the present invention, there is provided a production method of an electroform having a protruding pattern, comprising: a process of producing a mold using the production method described above; an electroforming process of forming a metal body on a recessed pattern of the mold using an electroforming method; and a peeling process of peeling the metal body from the mold.

According to another aspect of the present invention, there is provided a production method of a mold using an electroform, comprising: a process of producing an electroform using the production method described above; and a process of, by using the electroform having a protruding pattern, producing a mold which has a recessed pattern which is an inverted shape of the protruding pattern of the electroform and is made of a resin.

According to another aspect of the present invention, there is provided a manufacturing method of a pattern sheet having a protruding pattern, comprising: a process of producing a mold using the production method of an electroform described above; a supplying process of supplying a polymer solution to a recessed pattern of the mold; a drying process of drying the polymer solution to form a polymer sheet; and a peeling process of peeling the polymer sheet from the mold.

According to the production method of a mold, the manufacturing method of a pattern sheet, the production method of an electroform, and the production method of a mold using an electroform of the present invention, the generation of a step at the end portion of the recessed pattern can be suppressed.

BRIEF DESCRIPTION OF THE DRAWINGS

FIG. 8 is a view illustrating a process of forming a recessed pattern using the plate precursor illustrated in FIG. 2 in a thermoplastic resin sheet having a depression.

DESCRIPTION OF THE PREFERRED EMBODIMENTS

Figure 1A:
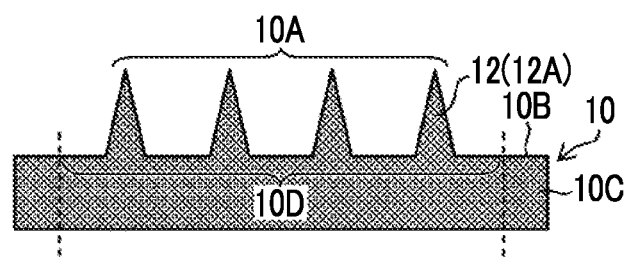
FIG. 1A is a diagram of a preparation process of preparing a plate precursor in a process procedure of a production method of a mold.

Hereinafter, preferred embodiments of the present invention will be described with reference to the accompanying drawings. The present invention is described by the following preferred embodiments.

Therefore, all modifications within the scope of the present invention are included in the appended claims.

Here, in the figures, like elements having similar functions are denoted by like reference numerals.

In addition, in this specification, in a case where a numerical value range is expressed using "to", the numerical value range includes the numerical values of the upper limit and the lower limit indicated by "to".

First Embodiment of Production Method of Mold

Hereinafter, in the surface of a thermoplastic resin sheet, a surface against which a protruding pattern of a plate precursor is pressed is referred to as a pressing surface. A first embodiment of a production method of a mold of the present invention is applied to a case where the pressing surface is flat, and a case where, when the plate precursor is pressed against the surface of the thermoplastic resin sheet, a part of a pattern presence region of the plate precursor excluding protrusions is stopped before reaching the flat pressing surface.

In addition, in the first embodiment, since the pressing surface X of a thermoplastic resin sheet 20 is flat and flush with a surface 203, the pressing surface X can also be referred to as the surface 20B.

The first embodiment of the present invention will be described with reference to the drawings. FIGS. 1A to 1E are process diagrams illustrating a procedure of the production method of a mold. In the first embodiment, an example in which a large mold 22 having a plurality of recessed patterns 20A is produced using a single plate precursor 10 will be described. FIG. 2 is a perspective view of the plate precursor.

Figure 2:
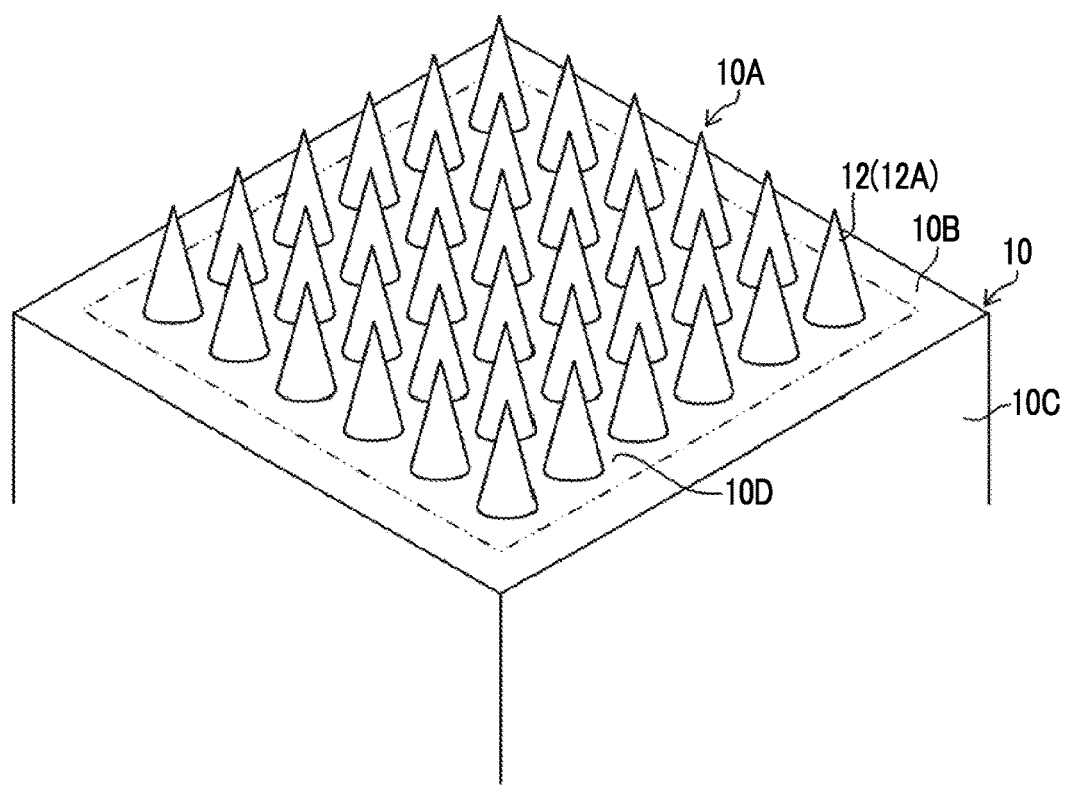
FIG. 2 is a perspective view of the plate precursor.

FIG. 1A illustrates a preparation process of preparing the plate precursor 10. As illustrated in FIGS. 1A and 2, the plate precursor 10 is constituted by a base 10C part and a protruding pattern 10A part, and the protruding pattern 10A is formed in a pattern presence region 10D on the base 10C.

Here, the pattern presence region 10D refers to a region where the protruding pattern 10A is present in the surface of the base 10C of the plate precursor 10 on the side having the protruding pattern 10A. The surface of the base 10C on the side having the protruding pattern 10A is formed into a flat surface 10B. The flat surface 10B may be a perfectly flat surface or may be a flat surface at first glance.

The plate precursor 10 has the protruding pattern 10A which is basically the same as a pattern sheet (a so-called formed product) having a protruding pattern to be produced.

The plate precursor 10 having the protruding pattern 10A is produced, for example, by machining a metal substrate, which is to become the plate precursor 10, using a cutting tool such as a diamond insert bite. As the metal substrate, stainless steel, an aluminum alloy, Ni, or the like may be used.

The protruding pattern 10A refers to a state in which protrusions 12 protruding in a direction away from the flat surface 10B of the plate precursor 10 are disposed on the flat surface 10B of the plate precursor 10. The number of the protrusions 12, the arrangement and positions of the protrusions 12, and the like are not limited.

As illustrated in FIGS. 1A and 2, in this embodiment, the protrusion 12 is constituted by a needle portion 12A which is tapered in the direction away from the flat surface 10B. The protrusion 12 is a so-called cone, and the cone includes a pyramid, a circular cone, and the like. In addition, FIGS. 1A and 2 are conceptual views of the plate precursor 10, and FIGS. 1A and 2 are different from each other in the number of protrusions 12 constituting the protruding pattern 10A.

For example, the protrusion 12 preferably has a height of 100 to 2000 μm from the flat surface 10B of the plate precursor 10 and has a distal end diameter of Φ50 μm or less. In the case where a plurality of the protrusions 12 are provided, it is preferable that the interval between adjacent protrusions 12 is 300 to 2000 μm. It is preferable that the aspect ratio (the height of the protrusion/the width of the bottom surface of the protrusion) of the protrusion 12 is 1 to 5.

Figure 1B:
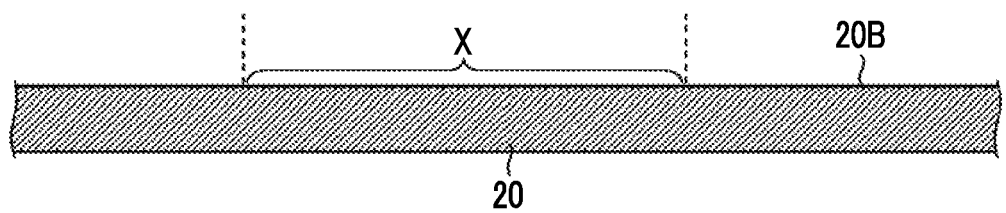
FIG. 1B is a diagram of a preparation process of preparing a thermoplastic resin sheet in the process procedure of the production method of a mold.

Next, FIG. 1B illustrates a preparation process of preparing a thermoplastic resin sheet. The thermoplastic resin sheet 20 as the material of the mold 22 is prepared, and the thermoplastic resin sheet 20 is set, for example, on a table (not illustrated).

For example, the thermoplastic resin sheet 20 has a thickness of 0.5 to 10 mm and a size of 100 mm×100 mm to 300 mm×300 mm, and has the surface 20B including the pressing surface X against which the protruding pattern 10A of the plate precursor 10 is to be pressed. The recessed patterns 20A to be described later are formed on the surface 20B side. It is preferable that the thickness of the thermoplastic resin sheet 20 is equal to or greater than at least the height of the protrusion 12 of the plate precursor 10.

The thermoplastic resin forming the thermoplastic resin sheet 20 is not particularly limited. For example, polyethylene terephthalate, polycarbonate, polymethyl methacrylate, polystyrene, polyethylene, a liquid crystal polymer, and polylactic acid may be suitably used. The thermoplastic resin sheet 20 means a thermoplastic resin in a state of having a small film thickness and a self-supporting property at room temperature. "Self-supporting property" means that a single body can hold its form without the support of other members.

Figure 1C:
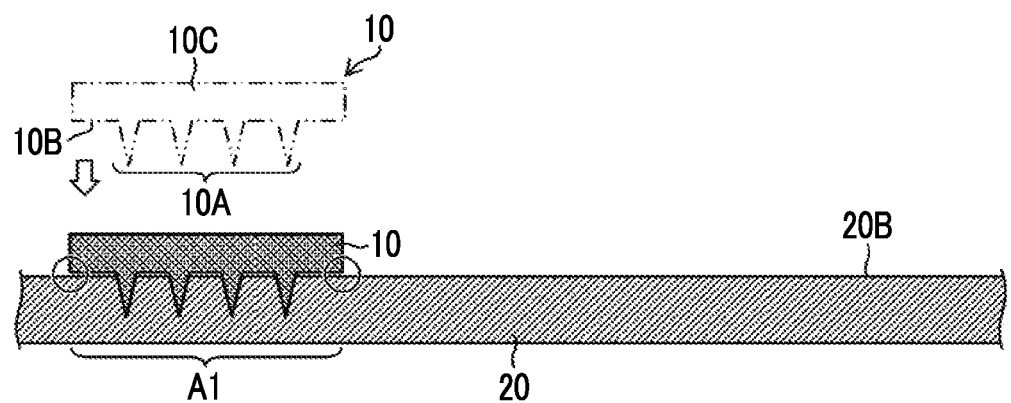
FIG. 1C is a diagram of an alignment process in the process procedure of the production method of a mold.
Figure 1D:
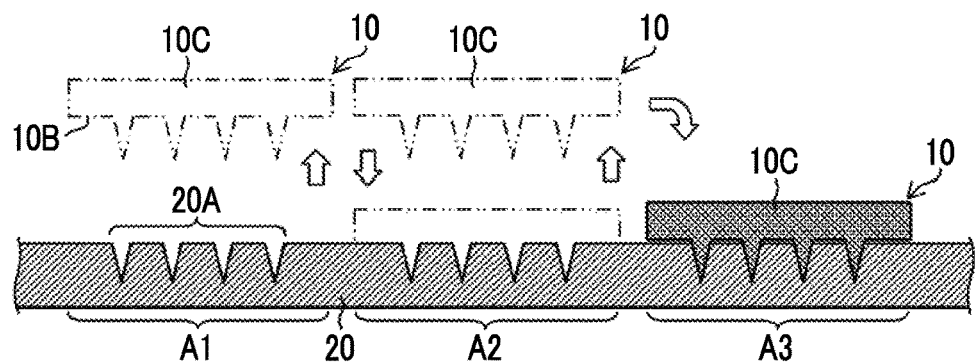
FIG. 1D is a diagram of a forming process in the process procedure of the production method of a mold.

FIGS. 1C and 1D show an alignment process, a forming process of forming a recessed pattern, and the alignment process and the forming process which are repeatedly performed. In a case of producing a small mold 22 having a single plate precursor 10 and a single recessed pattern 20A, there is no need to repeatedly perform the alignment process and the forming process.

First, a position (for example, a region A1) at which the plate precursor 10 is pressed against the thermoplastic resin sheet 20 is determined by moving the prepared plate precursor 10 and the thermoplastic resin sheet 20 relative to each other. For example, the alignment is performed by providing, for a table that supports the thermoplastic resin sheet 20, an X-axis drive mechanism and a Y-axis drive mechanism which move in directions perpendicular to each other on the horizontal plane.

For accurate alignment, for example, it is preferable to provide alignment marks for alignment on the surface 20B of the thermoplastic resin sheet 20. Furthermore, in order to detect the plate precursor 10, the thermoplastic resin sheet 20, and the alignment marks, it is preferable to provide an imaging device (charge-coupled device (CCD) camera) or the like.

Next, the heated plate precursor 10 is pressed against the surface 20B side of the thermoplastic resin sheet 20. Accordingly, the protrusions 12 forming the protruding pattern 10A of the plate precursor 10 are pressed against the thermoplastic resin sheet 20.

In the case where the plate precursor 10 is pressed against the surface 20B side of the thermoplastic resin sheet 20, the part of the pattern presence region 10D of the plate precursor 10 excluding the protrusions 12 is stopped before reaching the flat pressing surface X of the thermoplastic resin sheet 20. Accordingly, the flat surface 10B of the plate precursor 10 and the flat surface 20B of the thermoplastic resin sheet 20 are separated from each other. Therefore, not the entire pattern presence region 10D of the plate precursor 10 is pushed into the flat surface 20B of the thermoplastic resin sheet 20. Therefore, as indicated by the surrounding circles, the raising of thermoplastic resin sheet 20 at the end portions of the plate precursor 10 can be suppressed.

The plate precursor 10 is heated to a temperature at which the thermoplastic resin sheet 20 is softened. Heating is performed by a heater (not illustrated). The plate precursor 10 is heated to an appropriate temperature depending on the thermoplastic resin forming the thermoplastic resin sheet 20.

For example, a Z-axis drive mechanism which moves in the vertical direction is provided for the table (not illustrated) that supports the thermoplastic resin sheet 20 in order to press the protrusions 12 forming the protruding pattern 10A of the plate precursor 10 against the surface 20B side of the thermoplastic resin sheet 20. In a case where the Z-axis drive mechanism is provided for the table, the thermoplastic resin sheet 20 is moved toward the plate precursor 10.

Alternatively, the plate precursor 10 can also be attached by the Z-axis drive mechanism that moves in the vertical direction. In this case, the plate precursor 10 is moved toward the thermoplastic resin sheet 20.

While pressing the protrusions 12 of the heated plate precursor 10, the side of the surface 20B of the thermoplastic resin sheet 20 is heated for a certain period of time. Next, in a state in which the pressed protrusions 12 and the thermoplastic resin sheet 20 are brought into contact with each other, the plate precursor 10 is cooled until the thermoplastic resin sheet 20 is cooled to the softening temperature or lower.

Next, as illustrated in FIG. 1D, the plate precursor 10 and the thermoplastic resin sheet 20 are separated from each other, thereby forming the recessed pattern 20A having the inverted shape of the protruding pattern 10A on the surface 20B side of the thermoplastic resin sheet 20. The separation of the plate precursor 10 from the thermoplastic resin sheet 20 can be performed by the above-described Z-axis drive mechanism.

The recessed pattern 20A refers to a state in which recesses extending from the surface 20B of the thermoplastic resin sheet 20 toward the other surface are disposed on the surface 20B side of the thermoplastic resin sheet 20. The number of recesses, the arrangement of the recesses, the depth of the recesses, and the like are not limited. Since the recessed pattern 20A is the inverted shape of the protruding pattern 10A, the size, number, and arrangement of the recesses of the recessed pattern 20A are basically the same as those of the protrusions 12 pushed into the thermoplastic resin sheet 20.

In a case where the formation of the recessed pattern 20A in the region A1 is completed as illustrated in FIG. 1D, alignment (here, a region A2) between the plate precursor 10 and the thermoplastic resin sheet 20 is performed. In the region A2, the heated plate precursor 10 is pressed against the surface 20B side of the thermoplastic resin sheet 20. Accordingly, the protrusions 12 forming the protruding pattern 10A of the plate precursor 10 are pressed against the surface 20B side of the thermoplastic resin sheet 20.

As in the case of the region A1, in the region A2, the part of the pattern presence region 10D of the plate precursor 10 excluding the protrusions 12 is also stopped before reaching the flat pressing surface X of the thermoplastic resin sheet 20 in the case where the plate precursor 10 is pressed against the surface 20B side of the thermoplastic resin sheet 20.

In the region A2, while pressing the protrusions 12 of the heated plate precursor 10, the side of the surface 20B of the thermoplastic resin sheet 20 is heated for a certain period of time. Next, in a state in which the pressed protrusions 12 and the thermoplastic resin sheet 20 are brought into contact with each other, the plate precursor 10 is cooled until the thermoplastic resin sheet 20 is cooled to the softening temperature or lower. The plate precursor 10 and the thermoplastic resin sheet 20 are separated from each other, thereby forming the recessed pattern 20A having the inverted shape of the protruding pattern 10A on the surface 20B of the thermoplastic resin sheet 20.

Furthermore, in the case of the regions A1 and A2, in a region A3, alignment (here, the region A3) between the plate precursor 10 and the thermoplastic resin sheet 20 is performed, and the heated plate precursor 10 is pressed against the surface 20B of the thermoplastic resin sheet 20.

The alignment process of the plate precursor 10 and the thermoplastic resin sheet 20 and the forming process of forming the recessed pattern 20A having the inverted shape of the protruding pattern 10A of the plate precursor 10 on the thermoplastic resin sheet 20, which are described with reference to FIGS. 1C and 1D, are repeated.

Figure 1E:
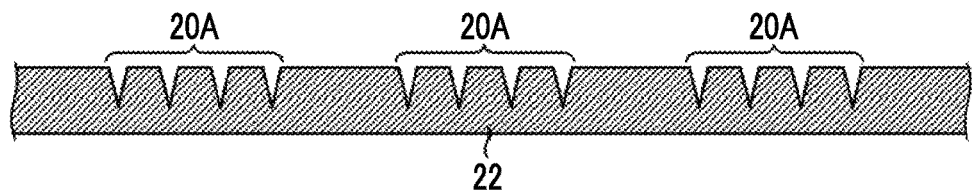
FIG. 1E is a view of the mold formed by the production method of a mold.

As illustrated in FIG. 1E, in a case where the formation of the predetermined recessed pattern 20A on the surface 20B side of the thermoplastic resin sheet 20 is completed, the mold 22 is produced from the thermoplastic resin sheet 20.

Figure 3:
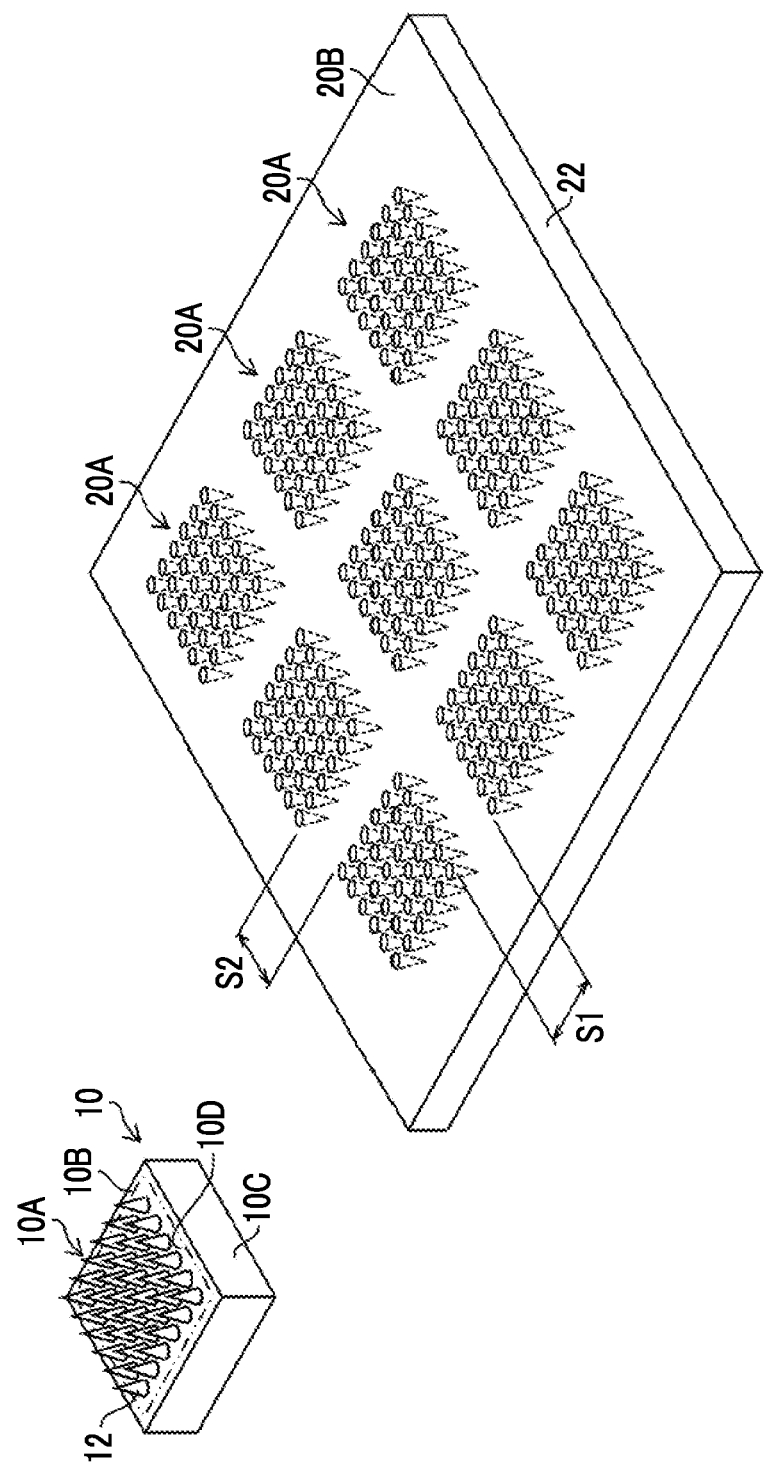
FIG. 3 is a perspective view of the plate precursor and the mold.

FIG. 3 is a perspective view of the plate precursor 10 and the mold 22. The mold 22 which has 3×3 recessed patterns 20A and is made of a resin is produced using the plate precursor 10 having one protruding pattern 10A. In this embodiment, in a case where the mold 22 which has 3×3 recessed patterns 20A and is made of a resin is produced, a large plate precursor having 3×3 protruding patterns is not produced. Therefore, in this embodiment, the number of operations for producing the plate precursor 10 can be reduced. Although the mold 22 which has 3×3 recessed patterns 20A and is made of a resin is exemplified, the number of recessed patterns 20A is appropriately determined.

Figure 23A:
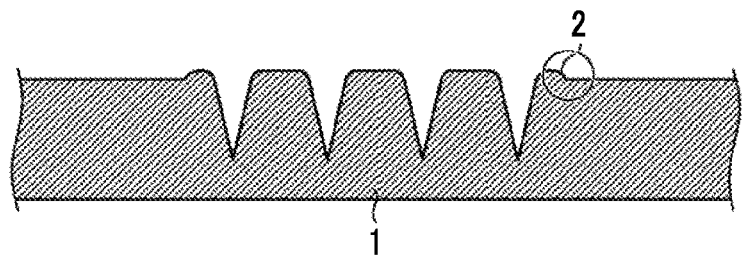
FIG. 23A is a view illustrating a step formed in the production of a mold.
Figure 23B:
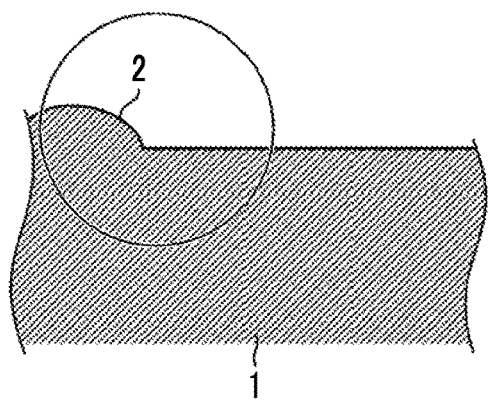
FIG. 23B is an enlarged view of the step.
Figure 24:
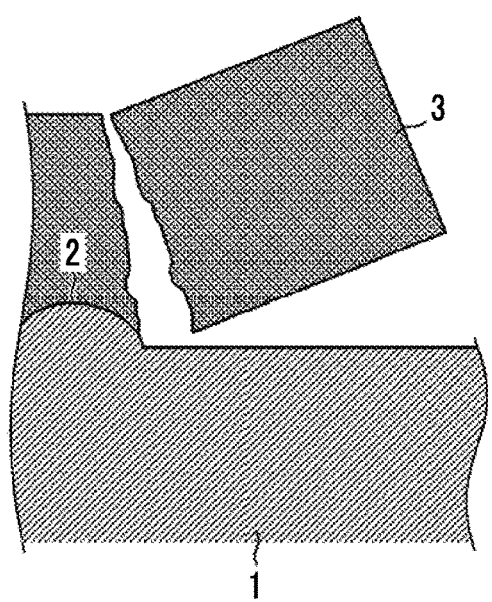
FIG. 24 is a view of breaking at the step in a case where a duplicate mold or formed product is peeled away from a mold.

Furthermore, in this embodiment, the generation of a step (see FIGS. 23A and 23B) between adjacent recessed patterns 20A (for example, S1 and S2) can be suppressed. That is, the surface 20B of the mold 22 becomes substantially flat. By causing the surface 20B of the mold 22 to be substantially flat, in a case where a formed product having a protruding pattern is produced using the mold 22, for example, the recessed pattern 20A of the mold 22 can be accurately filled with a polymer solution.

Figure 4:
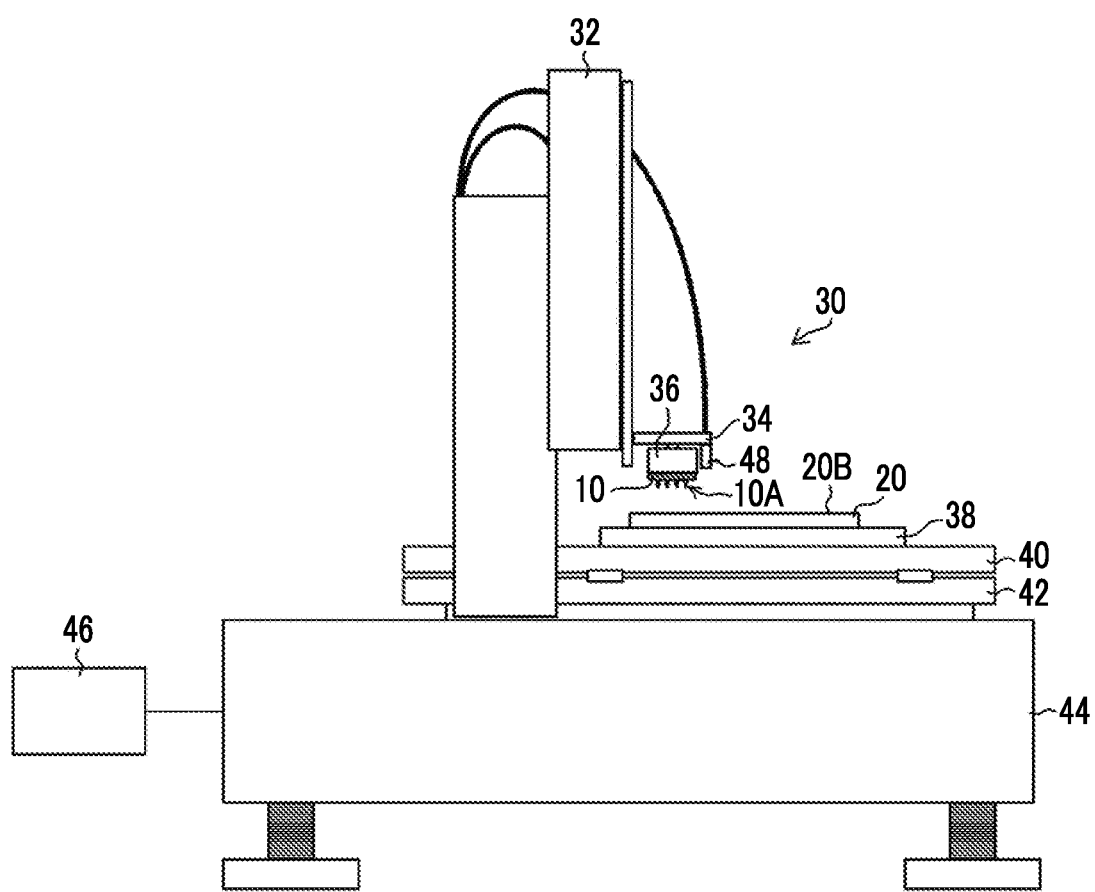
FIG. 4 is a schematic configuration diagram of an aligning apparatus.

Next, a method of controlling the plate precursor 10 in the case where the plate precursor 10 is pressed against the thermoplastic resin sheet 20 will be described. FIG. 4 is a schematic configuration diagram of an aligning apparatus. An aligning apparatus 30 includes a Z-axis drive mechanism 32 which drives the plate precursor 10 in a Z-axis direction, a connection portion 34 connected to the Z-axis drive mechanism 32, a holding portion 36 attached to the correction portion 34, a table 38 which supports the thermoplastic resin sheet 20, an X-axis drive mechanism 40 which drives the table 38 in an X-axis direction, a Y-axis drive mechanism 42 Which drives the table 38 in a Y-axis direction, a stand 44, a control system 46, and a laser displacement meter 48. In addition, the plate precursor 10 is held by the holding portion 36.

According to a first control method, first, alignment between the plate precursor 10 and the thermoplastic resin sheet 20 is performed by driving the X-axis drive mechanism 40 and the Y-axis drive mechanism 42.

In the case where the heated plate precursor 10 is pressed against the thermoplastic resin sheet 20, the position of the surface 20B of the thermoplastic resin sheet 20 is measured. That is, before moving the plate precursor 10, for example, the control system 46 measures the distance between the protruding pattern 10A of the plate precursor 10 and the surface 20B of the thermoplastic resin sheet 20 by using the laser displacement meter 48. By measuring the distance, the position of the surface 20B of the thermoplastic resin sheet 20 can be detected.

On the basis of the measured distance, the control system 46 determines the amount of the protruding pattern 10A pushed from the position of the surface 20B of the thermoplastic resin sheet 20. The control system 46 drives the Z-axis drive mechanism 32, and the Z-axis drive mechanism 32 moves the plate precursor 10 to the position of the surface 20B of the thermoplastic resin sheet 20 and further pushes the plate precursor 10 toward the thermoplastic resin sheet 20 side by a certain amount (the pushing amount determined).

According to a second control method, first, alignment between the plate precursor 10 and the thermoplastic resin sheet 20 is performed by driving the X-axis drive mechanism 40 and the Y-axis drive mechanism 42. The control system 46 drives the Z-axis drive mechanism 32, and the Z-axis drive mechanism 32 moves the plate precursor 10 to the position of the surface 20B of the thermoplastic resin sheet 20. The control system 46 measures the pressure applied to the plate precursor 10 while the plate precursor 10 is moved by the Z-axis drive mechanism 32. The pressure measurement method is not particularly limited. For example, a load cell may be disposed between the plate precursor 10 and the holding portion 36, and the pressure applied to the plate precursor 10 may be measured by the load cell. The load cell is a measuring instrument that can measure a compressive force in the thickness direction thereof.

The control system 46 compares the measured pressure with a preset pressure. In a case where the measured pressure reaches the preset pressure, the control system 46 determines that the protruding pattern 10A has reached the surface 20B of the thermoplastic resin sheet 20.

The control system 46 determines the amount of the protruding pattern 10A pushed from the position of the surface 20B of the thermoplastic resin sheet 20. The control system 46 drives the Z-axis drive mechanism 32 to push the plate precursor 10 toward the thermoplastic resin sheet 20 by a certain amount (the pushing amount determined).

According to a third control method, first, alignment between the plate precursor 10 and the thermoplastic resin sheet 20 is performed by the control system 46 by driving the X-axis drive mechanism 40 and the Y-axis drive mechanism 42. The control system 46 drives the Z-axis drive mechanism 32, and the Z-axis drive mechanism 32 moves the plate precursor 10 to the position of the surface 20B of the thermoplastic resin sheet 20. The control system 46 measures the pressure applied to the plate precursor 10 while the plate precursor 10 is moved by the Z-axis drive mechanism 32.

The control system 46 compares the measured pressure with a preset pressure. In the third control method, the relationship between the pressure applied to the plate precursor 10 and the amount (depth) of the protruding pattern 10A pushed into the thermoplastic resin sheet 20 is previously obtained.

The control system 46 compares the measured pressure with a preset pressure. In a case where the measured pressure reaches the set pressure, the control system 46 determines that the protruding pattern 10A has reached a desired pushing amount from the surface 20B of the thermoplastic resin sheet 20. In this embodiment, the control system 46 calculates the pushing amount from the previously obtained relationship based on the measured pressure.

In a case where the pushing amount calculated from the pressure is a desired pushing amount with respect to the thermoplastic resin sheet 20, the plate precursor 10 is not pushed into the thermoplastic resin sheet 20. That is, the control system 46 measures a pressure applied to the plate precursor 10, compares the measured pressure with a certain pressure value which is set, and determines the pushing amount of the plate precursor 10 as "0".

In a case where the pushing amount calculated from the pressure is smaller than the desired pushing amount with respect to the thermoplastic resin sheet 20, the control system 46 determines the amount of the protruding pattern 10A of the plate precursor 10 pushed into the thermoplastic resin sheet 20 based on the current position of the plate precursor 10. The control system 46 drives the Z-axis drive mechanism 32 to push the plate precursor 10 toward the thermoplastic resin sheet 20 by a certain amount (the pushing amount determined).

According to the above-described control methods, it becomes possible to accurately push the protrusions 12 forming the protruding pattern 10A of the plate precursor 10 into the thermoplastic resin sheet 20. Accordingly, the part of the pattern presence region 10D of the plate precursor 10 excluding the protrusions 12 can be accurately stopped before reaching the flat pressing surface X of the thermoplastic resin sheet 20.

Next, the plate precursor 10 having the protrusions 12 with a shape that is different from the shape of the protrusions 12 forming the protruding pattern of the plate precursor 10 illustrated in FIG. 2 and further suppresses the generation of a step will be described.

Figure 5A:
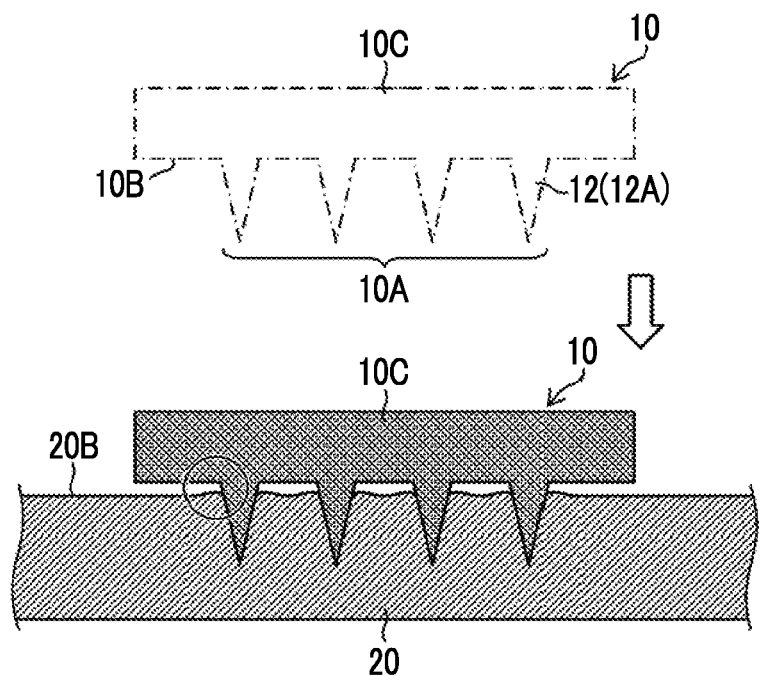
FIG. 5A is a view illustrating raised portions in a process of producing a mold using the plate precursor illustrated in FIG. 2.

FIG. 5A is a view illustrating a case of producing the mold 22 using the plate precursor 10 illustrated in FIG. 2. As illustrated in FIG. 5A, the protrusion 12 included in the protruding pattern 10A of the plate precursor 10 is constituted by a needle portion 12A which is tapered in the direction away from the flat surface 10B.

Figure 5B:
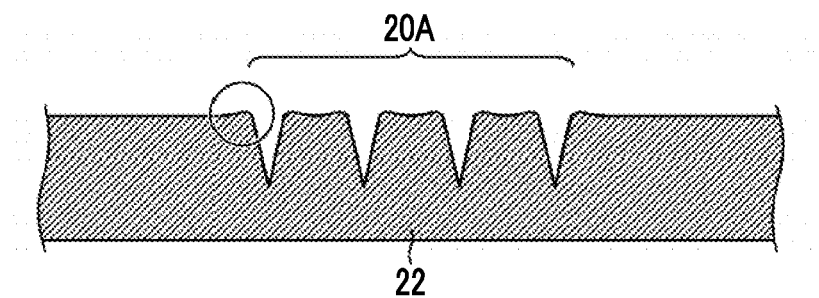
FIG. 5B is a view of the mold having the raised portions in the process of producing a mold using the plate precursor illustrated in FIG. 2.

Therefore, as illustrated in FIG. 5A, although depending on the shape of the protrusion 12, as indicated by the surrounding circle, there may be cases where the surface 20B of the thermoplastic resin sheet 20 is raised at the root portion of the protrusion 12. In a case where the thermoplastic resin sheet 20 is cooled in this state, as illustrated in FIG. 5B, there is concern that steps may be generated on the surface 20B in the region of the recessed pattern 20A of the mold 22.

That is, as described below, in the production method of a mold of the first embodiment, the generation of steps can be further suppressed by changing the shape of the protrusions 12 constituting the protruding pattern 10A of the plate precursor 10.

Here, as described above, the step means a protrusion that protrudes from the surface 20B to an extent that the flatness of the surface 20B of the thermoplastic resin sheet 20 is affected. There may be cases where the step affects the productivity in a case where a formed product is manufactured or the precision of the formed product.

Figure 6A:
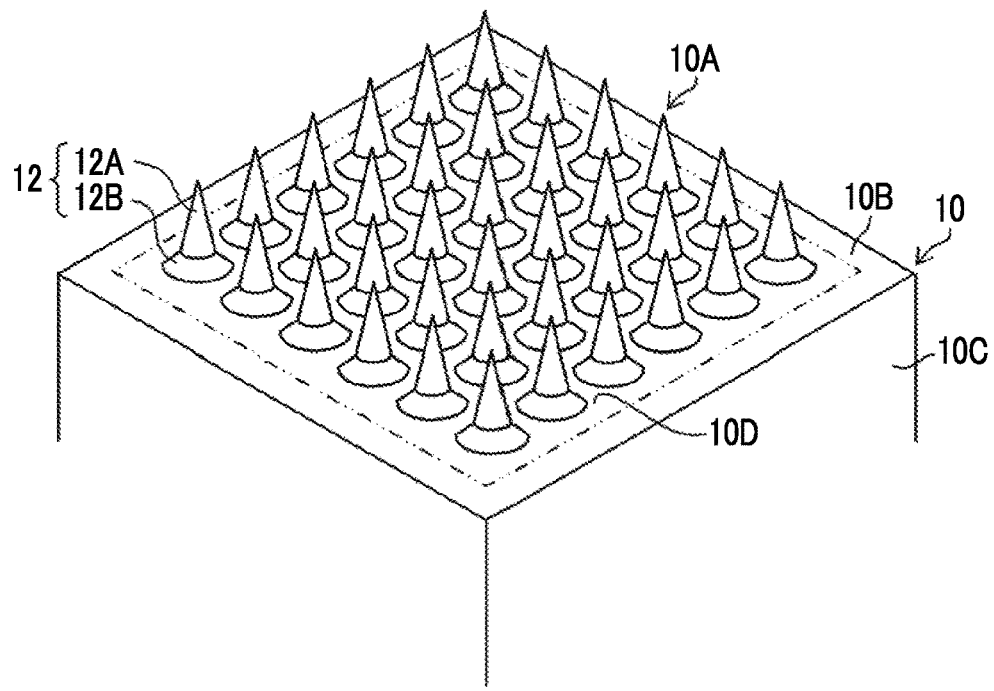
FIG. 6A is a perspective view of a plate precursor having a different protrusion shape from that in FIG. 2.
Figure 6B:
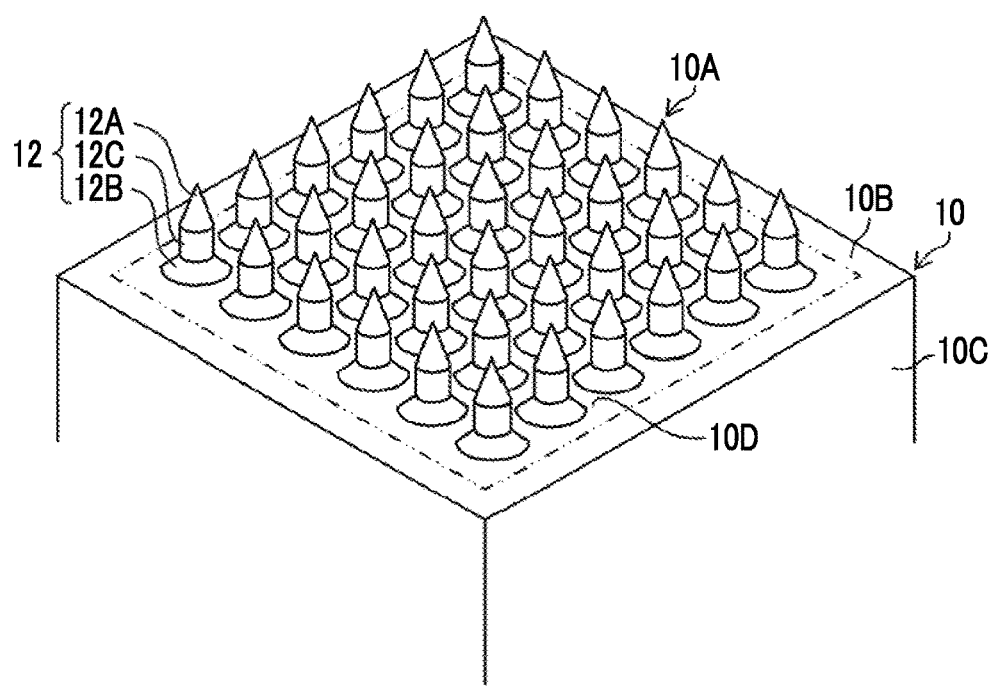
FIG. 6B is a perspective view of another embodiment of the plate precursor having a different protrusion shape from that in FIG. 2.

On the other hand, FIGS. 6A and 6B illustrate the plate precursor 10 in which the shape of the protrusion 12 is different from that in FIG. 2.

The protrusion 12 included in the protruding pattern 10A illustrated in FIG. 6A is constituted by a frustum portion 12B and the tapered needle portion 12A in the direction away from the flat surface 10B. The frustum portion 12B includes a square frustum, a circular cone frustum, and the like. Another frustum portion may be included between the frustum portion 12B and the needle portion 12A.

For example, the protrusion 12 preferably has a height of 100 to 2000 μm from the flat surface 10B of the plate precursor 10 and has a distal end diameter of Φ50 μm or less. In the case where a plurality of the protrusions 12 are provided, it is preferable that the interval between adjacent protrusions 12 is 300 to 2000 μm. It is preferable that the aspect ratio (the height of the protrusion/the width of the bottom surface of the protrusion) of the protrusion 12 is 1 to 5.

The ratio of the height of the needle portion 12A to the height of the frustum portion 12B (the height of the needle portion 12A/the height of the frustum portion 12B) is preferably 1 to 10. The angle between the side surface of the frustum portion 12B and the flat surface 10B is preferably 10° to 60°.

In addition, the protrusion 12 included in the protruding pattern 10A of the plate precursor 10 illustrated in FIG. 6B is constituted by the frustum portion 12B, a columnar portion 12C, and the needle portion 12A which is tapered, in the direction away from the flat surface 10B. Here, the columnar portion 12C means a shape having two opposing parallel bottom surfaces, as represented by a cylinder or a rectangular parallelepiped, in which the areas of the two bottom surfaces are the same.

For example, the protrusion 12 preferably has a height of 100 to 2000 μm from the flat surface 10B of the plate precursor 10 and has a distal end diameter of Φ50 μm or less. In the case where a plurality of the protrusions 12 are provided, it is preferable that the interval between adjacent protrusions 12 is 300 to 2000 μm. It is preferable that the aspect ratio (the height of the protrusion/the width of the bottom surface of the protrusion) of the protrusion 12 is 1 to 5.

The ratio of the total height of the needle portion 12A and the columnar portion 12C to the height of the frustum portion 12B (the total height of the needle portion 12A and the columnar portion 12C/the height of the frustum portion 12B) is preferably 1 to 10. In addition, the ratio of the height of the needle portion 12A to the height of the columnar portion 12C (the height of the needle portion 12A/the height of the columnar portion 12C) is preferably 0.25 to 10. The angle between the side surface of the needle portion 12A and the flat surface 10B is preferably 45° to 85°. Furthermore, the angle between the side surface of the frustum portion 12B and the flat surface 10B is preferably 10° to 60°.

Figure 7A:
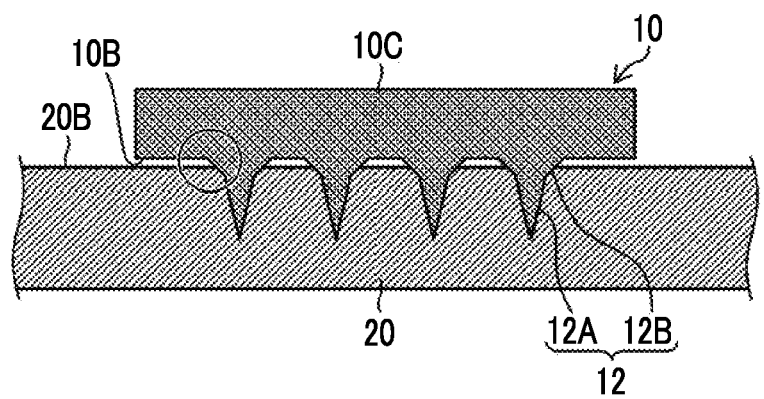
FIG. 7A is a view illustrating a state in which the plate precursor illustrated in FIG. 6A is pressed against the thermoplastic resin sheet.
Figure 7B:
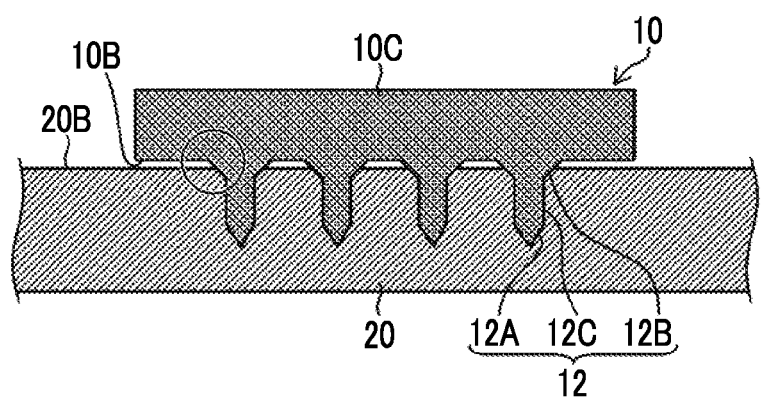
FIG. 7B is a view illustrating a state in which the plate precursor illustrated in FIG. 6B is pressed against the thermoplastic resin sheet.

FIGS. 7A and 7B illustrate states in which the plate precursors 10 illustrated in FIGS. 6A and 6B are pressed against the thermoplastic resin sheet 20. In FIG. 7A, the plate precursor 10 having the protrusion 12 constituted by the frustum portion 12B, and the tapered needle portion 12A, in the direction away from the flat surface 10B illustrated in FIG. 6A is used. As illustrated in FIG. 7A, in the case where the plate precursor 10 is pressed against the thermoplastic resin sheet 20, by bringing the frustum portion 12B of the protrusion 12 into contact with the surface 20B of the thermoplastic resin sheet 20, the raising of the surface 20B of the thermoplastic resin sheet 20 is suppressed as indicated by the surrounding circle.

In FIG. 7B, the plate precursor 10 having the protrusion 12 constituted by the frustum portion 12B, the columnar portion 12C, and the tapered needle portion 12A, in the direction away from the flat surface 10B illustrated in FIG. 6B is used. As illustrated in FIG. 7B, in the case where the plate precursor 10 is pressed against the thermoplastic resin sheet 20, by bringing the frustum portion 12B of the protrusion 12 into contact with the surface 20B of the thermoplastic resin sheet 20, raising of the surface 20B of the thermoplastic resin sheet 20 is suppressed as indicated by the surrounding circle.

Next, a second embodiment of the production method of a mold as another method to solve the concern of the step described with reference to FIG. 5 will be described.

Second Embodiment of Production Method of Mold

The second embodiment of the production method of a mold of the present invention refers to a case where the surface of the thermoplastic resin sheet 20 is the pressing surface X against which the protruding pattern 10A of the plate precursor 10 is pressed and a depression 24 is formed in the pressing surface X in advance. In other words, as illustrated in FIG. 8, the second embodiment refers to a case where the depression 24 is formed in the region where the recessed pattern 20A is formed. That is, the pressing surface X is the region where the recessed pattern 20A is formed in the surface 20B of the thermoplastic resin sheet 20 against which the protrusions 12 forming the protruding pattern 104 of the plate precursor 10 are pressed.

Figure 9:
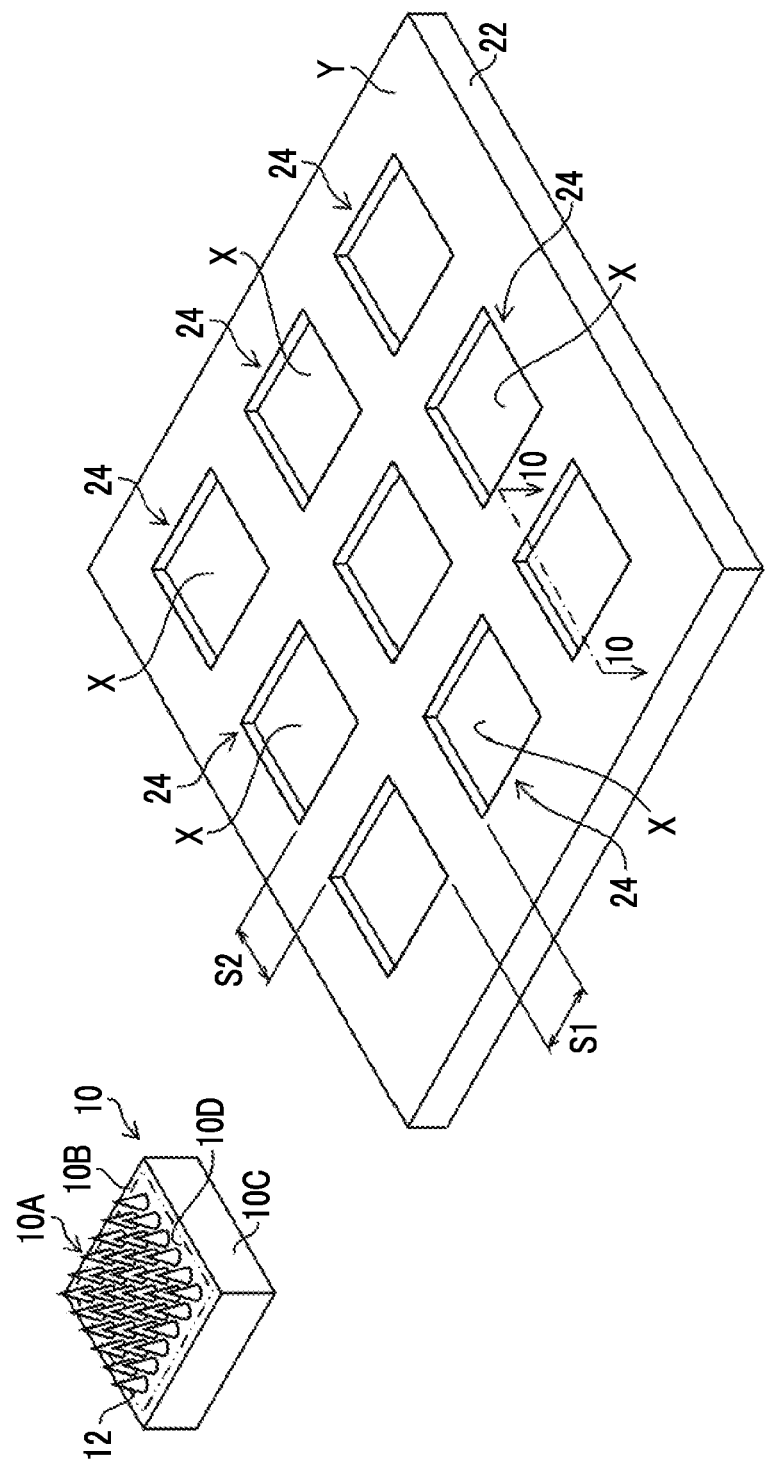
FIG. 9 is a perspective view illustrating the plate precursor and depressions formed in the thermoplastic resin sheet.
Figure 10:
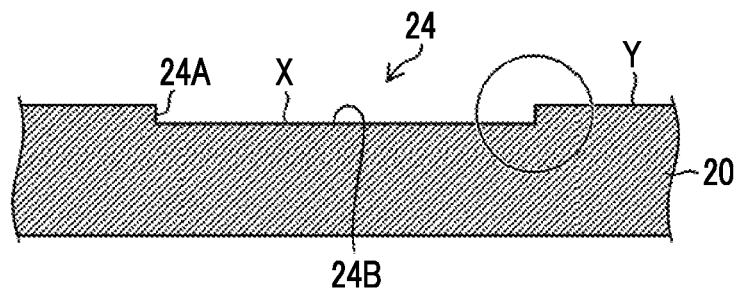
FIG. 10 is a sectional view taken the line 10-10 of FIG. 9.

FIG. 9 is a view corresponding to FIG. 3, and refers to a case where the depressions 24 are formed in advance in the nine (3×3) pressing surfaces X in which the protruding patterns 20A of the thermoplastic resin sheet 20 are to be formed. Accordingly, the surface of the thermoplastic resin sheet 20 is constituted by the pressing surfaces X in which the depression 24 is formed and a flat outer surface Y in which the depression 24 is not formed. In the case of FIG. 9, the mold 22 which has 3×3 recessed patterns 20A and is made of a resin can be produced using the plate precursor 10 having one protruding pattern 10A. In addition, FIG. 10 is a sectional view taken along the line 10-10 of FIG. 9 and the region corresponding to the pattern presence region 10D of the plate precursor 10.

The depression 24 may be the depression 24 having an arc hole shape as illustrated in FIG. 8. However, as illustrated in FIGS. 9 and 10, the depression 24 having a rectangular hole shape constituted by a bottom surface 24B which is the flat pressing surface X and a side surface 24A is preferable, and the following description will be provided using the depression 24 having a rectangular hole shape as an example.

Figure 11A:
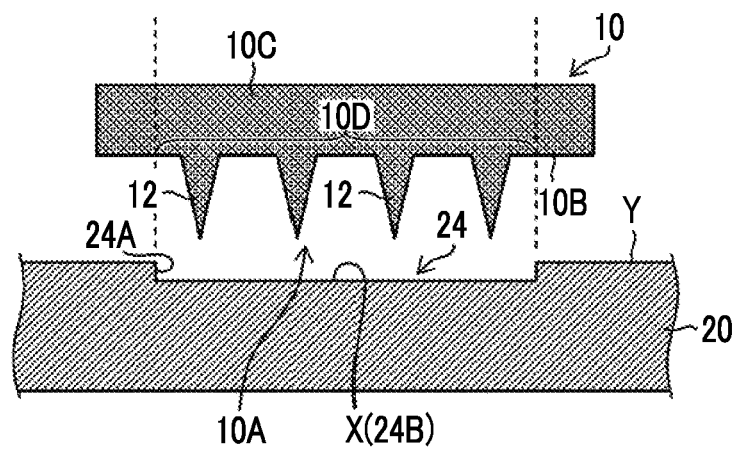
FIG. 11A is a sectional view of a preparation process of preparing the plate precursor and the thermoplastic resin sheet having the depression.
Figure 11B:
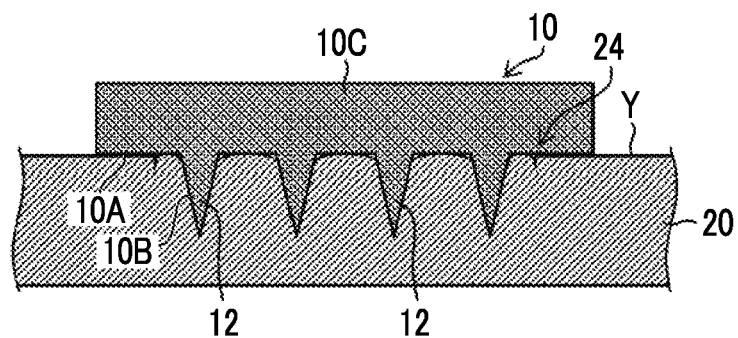
FIG. 11B is a sectional view of an alignment process and a forming process in which the plate precursor is aligned with and pressed against the depression of the thermoplastic resin sheet.
Figure 11C:
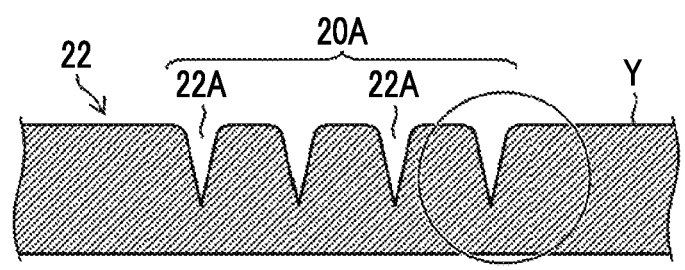
FIG. 11C is a sectional view illustrating the formed mold with no step.
Figure 11D:
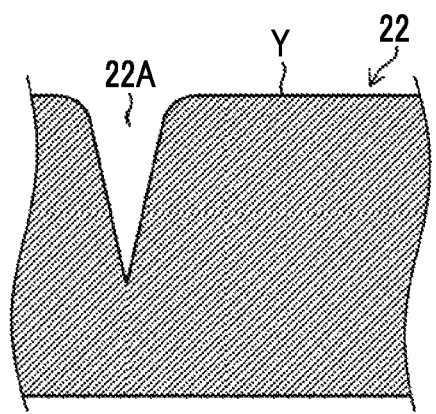
FIG. 11D is an enlarged sectional view of a mold end portion of the formed mold.

FIGS. 11A to 11C are process diagrams illustrating a procedure of the production method of a mold in which the thermoplastic resin sheet 20 having the depression 24 with a rectangular hole shape formed therein is used. FIG. 11D is an enlarged view of a mold end portion of the produced mold 22.

As illustrated in FIG. 11A, the plate precursor 10 having the protruding pattern 10A on the flat surface 10B, and the thermoplastic resin sheet 20 in which the depression 24 is formed in the pressing surface X in which the recessed pattern 20A is to be formed are prepared (preparation process). In addition, the position at which the plate precursor 10 is to be pressed against the thermoplastic resin sheet 20 is determined by moving the plate precursor 10 and the thermoplastic resin sheet 20 relative to each other to cause the protruding pattern 10A of the plate precursor 10 to be positioned immediately above the pressing surface X of the thermoplastic resin sheet 20 (alignment process).

Next, as shown in FIG. 11B, the heated plate precursor 10 is pressed against the thermoplastic resin sheet 20. In this case, the flat surface 10B of the plate precursor 10 and the outer surface Y of the thermoplastic resin sheet 20 are brought into close contact with each other. Next, after the plate precursor 10 is cooled while the plate precursor 10 is pressed, the plate precursor 10 and the thermoplastic resin sheet 20 are separated from each other, thereby forming the recessed pattern 20A having the inverted shape of the protruding pattern 10A on the thermoplastic resin sheet 20 (forming process).

In addition, the alignment process and the forming process are repeatedly performed for the nine depressions 24.

In the process of producing the mold described above, in the case where the plate precursor 10 is pressed against the thermoplastic resin sheet 20, as illustrated in FIG. 11B, the pressing surface X of the thermoplastic resin sheet 20 is raised. However, since the depression 24 is formed in advance in the thermoplastic resin sheet 20, even though the pressing surface X of the thermoplastic resin sheet 20 is raised, the raised portion is absorbed by the depression 24, and the generation of a step is suppressed. The size (volume) of the depression 24 is appropriately set in consideration of the size of the raised portion of the pressing surface X in a case Where the protrusions 12 of the plate precursor 10 are pushed into the thermoplastic resin sheet 20.

Therefore, as illustrated in FIG. 11C, the flatness of the outer surface Y of the thermoplastic resin sheet 20 is maintained. Accordingly, as illustrated in FIG. 11D, the formation of steps at the end portions of the recessed pattern 20A of the mold 22 in which needle-like recesses 22A are two-dimensionally arranged can be suppressed.

That is, in the second embodiment of the production method of a mold, by forming the depression 24 in the pressing surface X of the thermoplastic resin sheet 20, the formation of steps caused by pressing the plate precursor 10 against the thermoplastic resin sheet 20 at a position at which the flat surface 10B of the plate precursor 10 and the pressing surface X of the thermoplastic resin sheet 20 are separated from each other is suppressed.

Figure 12:
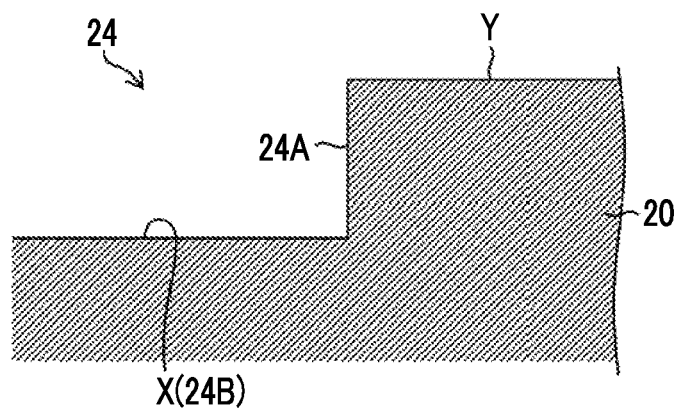
FIG. 12 is a sectional view illustrating a rectangular depression formed in the thermoplastic resin sheet.

FIG. 12 is an enlarged view illustrating an end portion surrounded by the circle in the depression 24 having a rectangular hole shape in FIG. 10.

In the forming process described above, in a case where the heating temperature of the plate precursor 10 is equal to or higher than the melting point of the thermoplastic resin sheet 20 and the recessed pattern 20A is transferred by the flow of the melted resin, as illustrated in FIG. 12, the depression 24 having a rectangular vertical sectional shape in which the side surface 24A is provided at a right angle to the bottom surface 24B (the pressing surface X) of the depression is preferable.

Figure 13:
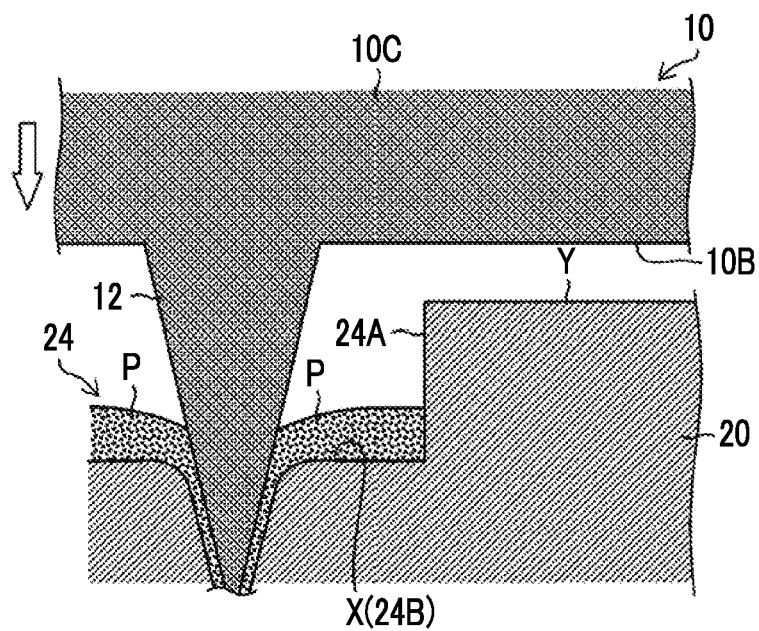
FIG. 13 is a schematic view illustrating the flow of a melted resin in a case where the plate precursor is pressed against the rectangular depression.

This is because, as illustrated in the schematic view of FIG. 13, in the case where the protrusion 12 of the plate precursor 10 heated to a temperature equal to or higher than the melting point of the thermoplastic resin sheet 20 is pushed into the thermoplastic resin sheet 20, the thermoplastic resin sheet 20 in the periphery of the protrusion 12 is melted. The melted resin P is pushed away by the pressing force of the protrusion 12 and flows into the depression 24. In this case, in the case where the depression 24 is rectangular, the melted resin P flowing into the depression 24 is blocked by the side surface 24A of the depression 24. This makes it difficult for the melted resin P to flow to the outer surface Y of the thermoplastic resin sheet 20. Therefore, the formation of steps at the mold end portions of the produced mold 22 can be further suppressed.

Figure 14:
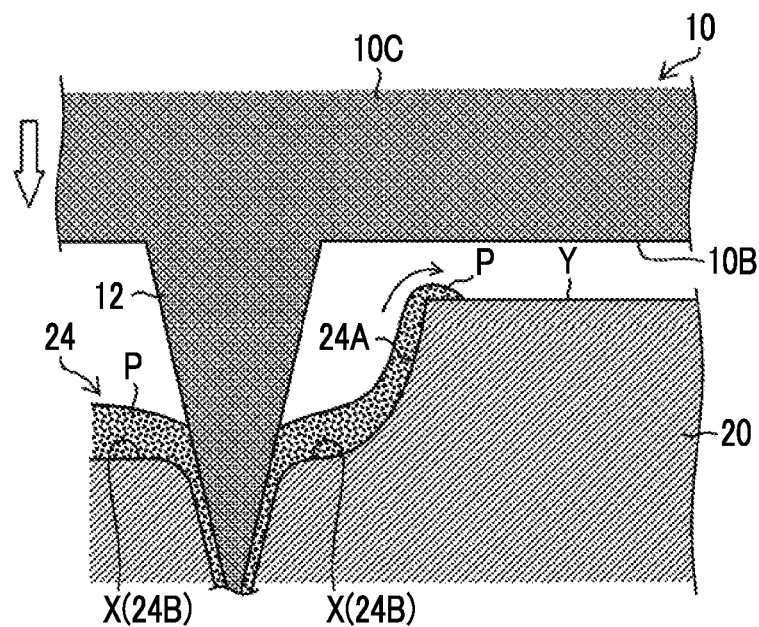
FIG. 14 is a schematic view illustrating the flow of a melted resin in a case where the plate precursor is pressed against an arcuate depression.

Contrary to this, as illustrated in the schematic view of FIG. 14, in a case of the depression 24 having the side surface 24A which is curved with respect to the bottom surface 24B (the pressing surface X), in other words, having an arcuate vertical sectional shape, there may be cases where the melted resin P flowing into the depression 24 climbs up the side surface 24A of the depression 24 and flows to the outer surface Y of the thermoplastic resin sheet 20.

Accordingly, there may be cases where steps are formed at the end portions of the recessed pattern 20A of the produced mold 22.

Figure 15:
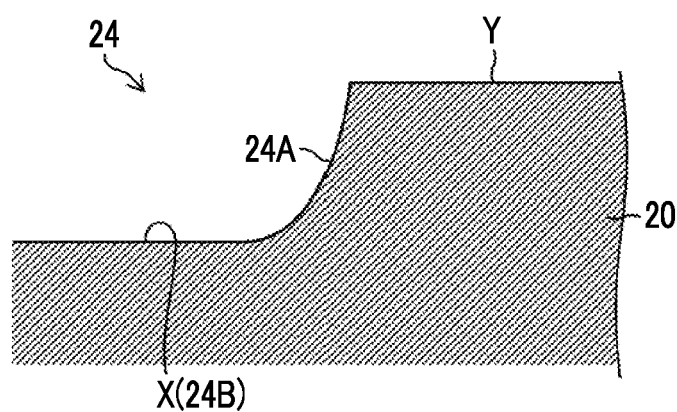
FIG. 15 is a sectional view illustrating the arcuate depression formed in the thermoplastic resin sheet.

On the other hand, in a case where the heating temperature of the plate precursor 10 is equal to or lower than the melting point of the thermoplastic resin sheet 20 and the recessed pattern 20A is transferred by plastic deformation of the thermoplastic resin sheet 20, as illustrated in FIG. 15, the depression 24 having the side surface 24A which is curved with respect to the bottom surface 24B (the pressing surface X) (having an arcuate vertical sectional shape) is preferable.

Figure 16:
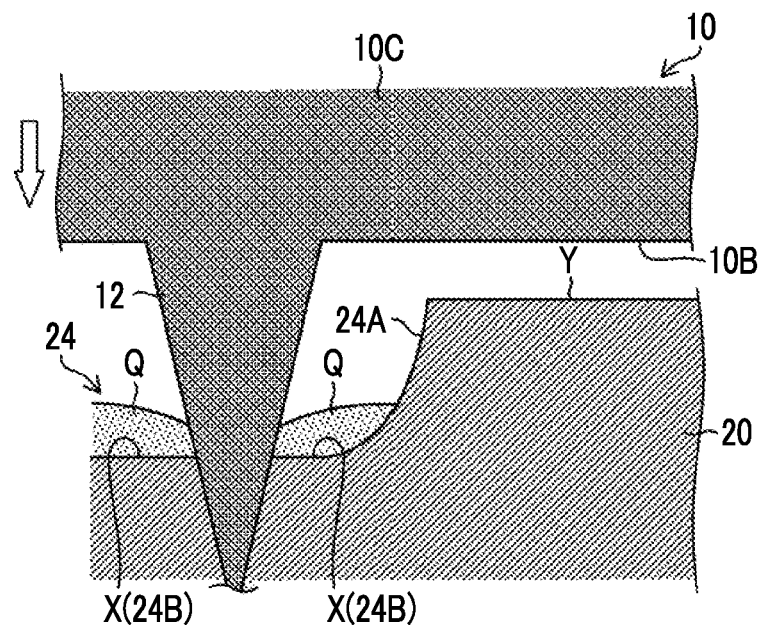
FIG. 16 is a schematic view illustrating raised portions of the resin in a case where the plate precursor is pressed against the arcuate depression.

This is because, as illustrated in the schematic view of FIG. 16, in the case where the protrusion 12 of the plate precursor 10 heated to a temperature equal to or lower than the melting point of the thermoplastic resin sheet 20 is pushed into the thermoplastic resin sheet 20, the thermoplastic resin sheet 20 is plastically deformed and the pressing surface X is raised. In this case, in the case where the depression 24 is arcuate, the pressing surface X is raised along the curved side surface 24A, and raised portions Q which are raised throughout the entire space between the protrusions 12 and the depression 24 are easily formed. Accordingly, it is easy to effectively use the space of the depression 24 which absorbs the raised portions of the thermoplastic resin sheet 20, and it becomes difficult for the raised portion Q to reach the outer surface Y of the thermoplastic resin sheet 20. Therefore, the formation of steps at the end portions of the recessed pattern 20A of the produced mold 22 can be further suppressed.

Figure 17:
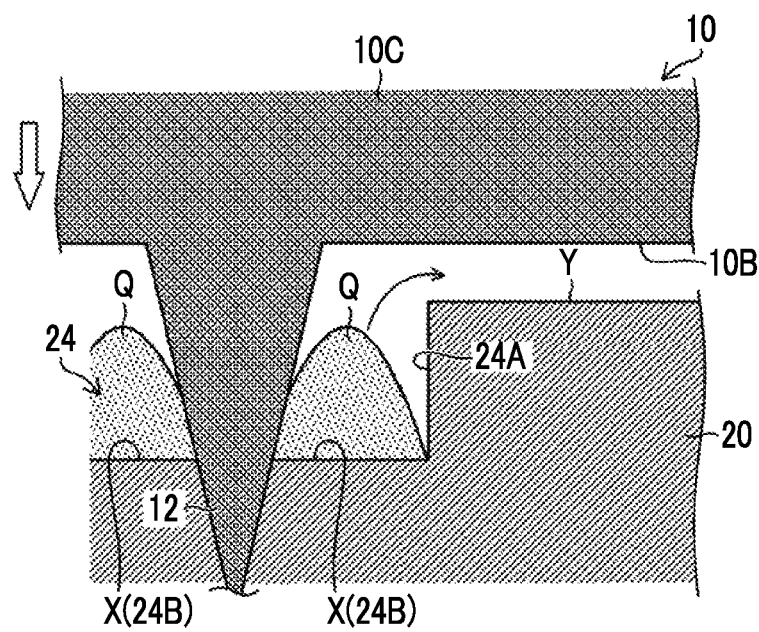
FIG. 17 is a schematic view illustrating raised portions of the resin in a case where the plate precursor is pressed against the rectangular depression.

Contrary to this, as illustrated in the schematic view of FIG. 17, in a case of the rectangular depression 24, the raising force is more likely to be cut off by the side surface 24A at a right angle than the arcuate shape, and the raised portions Q having a mountain shape are easily formed in the space between the protrusions 12 and the depression 24. Accordingly, it is difficult to effectively use the space of the depression 24 that absorbs the raised portion of the thermoplastic resin sheet 20, so that there may be cases where the raised portion Q reaches the outer surface Y of the thermoplastic resin sheet 20. Therefore, there may be cases where steps are formed at the end portions of the recessed pattern 204 of the produced mold 22.

The aligning apparatus 30 and the control method described in the first embodiment can also be applied to the second embodiment. Furthermore, it is preferable that as in the first embodiment, the plate precursor 10 having the protrusions 12 having the shapes described with reference to FIGS. 6A and 6B is used in the second embodiment.

Next, a manufacturing method of a pattern sheet having a protruding pattern which is an example of a formed product having a fine pattern using the mold 22 produced in the first embodiment or the second embodiment will be described. FIGS. 184 to 18G are process diagrams illustrating a procedure of the manufacturing method of a pattern sheet using the mold 22.

Figure 18A:
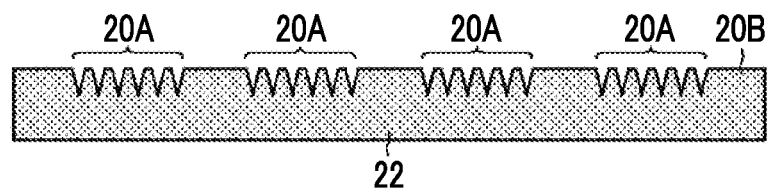
FIG. 18A is a diagram illustrating preparation of a mold in a process procedure of a manufacturing method of a pattern sheet using a mold.

FIG. 18A illustrates a state in which the mold 22 is prepared. The mold 22 is produced by the production method of a mold described above, and the recessed patterns 20A are formed on the surface 20B of the mold 22.

Figure 18B:
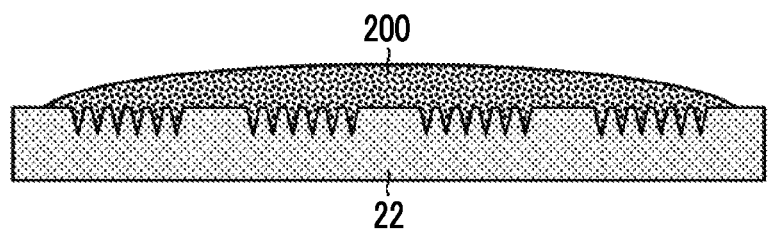
FIG. 18B is a diagram illustrating supply of a polymer solution to a recessed pattern in the process procedure of the manufacturing method of a pattern sheet using a mold.

FIG. 18B illustrates a supplying process of supplying a polymer solution to the recessed patterns 20A of the mold 22.

First, a polymer solution 200 is prepared. As a material of the resin polymer used for the polymer solution 200, it is preferable to use a biocompatible resin. As such resins, sugars such as glucose, maltose, pullulan, sodium chondroitin sulfate, sodium hyaluronate, hydroxyethyl starch, and hydroxypropyl cellulose, proteins such as gelatin, and biodegradable polymers such as polylactic acid and a lactic acid-glycolic acid copolymer are preferably used. Among these, since gelatin-based materials have adhesion to many base materials and have a strong gel strength in a case of being used as a gelating material, the gelatin-based materials can be brought into close contact with a base material in a peeling process, which will be described later, and a polymer sheet can be peeled away from the mold 22 using the base material, so that the gelatin-based materials can be suitably used.

Furthermore, a drug may be contained in the polymer solution 200. The drug to be contained in the polymer solution 200 is not particularly limited as long as the drug is a substance having a physiological activity. The drug is preferably selected from peptides, proteins, nucleic acids, polysaccharides, vaccines, pharmaceutical compounds, or cosmetic ingredients. In addition, it is preferable that the pharmaceutical compound belongs to a water-soluble low molecular weight compound. Here, the low molecular weight compound is a compound having a molecular weight range of several hundreds to several thousands.

Although the concentration varies depending on the material, it is preferable that the concentration is set so that the resin polymer is contained at 10 to 50 mass % in the polymer solution 200 which does not contain the drug. The solvent used for dissolution may be warm water or may be volatile, and methyl ethyl ketone, alcohol, or the like may be used. In addition, it is possible to dissolve the drug, which is supplied into the body according to the application, in the solution of the polymer resin. The polymer concentration of the polymer solution 200 containing the drug (the concentration of the polymer excluding the drug in a case where the drug itself is a polymer) is preferably in a range of 0 to 40 mass %.

As a method of preparing the polymer solution 200, in a case where a water-soluble polymer (such as gelatin) is used, a water-soluble powder may be dissolved in water and the drug may be added after the dissolution. Otherwise, a powder of a water-soluble polymer may be dissolved in a liquid in which the drug is dissolved. In a case where it is difficult to dissolve the polymer in water, heating may be performed for dissolution. The temperature can be appropriately selected depending on the kind of the polymer material, and it is preferable that heating is performed at a temperature of about 60° C. or lower. For the solution containing the drug, the viscosity of the solution of the polymer resin is preferably 100 Pa·s or less, and more preferably 10 Pa·s or less. For a solution which does not contain a drug, the viscosity is preferably 2000 Pa·s or less, and more preferably 1000 Pa·s or less. By appropriately adjusting the viscosity of the solution of the polymer resin, injecting the solution into a needle-like recess of a mold is facilitated. For example, the viscosity of the solution of the polymer resin can be measured with a capillary viscometer, a falling ball viscometer, a rotational viscometer, or a vibrational viscometer.

As illustrated in FIG. 18B, the polymer solution 200 is supplied to the mold 22 such that the recessed patterns 20A are filled with the polymer solution 200. That is, the recesses constituting the recessed patterns 20A are filled with the polymer solution 200.

As a method for filling the recessed patterns 20A with the polymer solution 200, a method of performing filling using a spin coater, a method of performing filling by moving a squeegee, a method of performing filling while moving a slit nozzle, a method of filling the recesses of the recessed patterns 20A using a dispenser, or the like may be employed.

As disclosed in WO2014/077242, it is preferable that in a state in which the slit nozzle is brought into contact with the surface of the mold 22, the polymer solution 200 is supplied to the recessed patterns 20A while moving the slit nozzle and the mold 22 relative to each other. In the case where the slit nozzle and the mold 22 are moved relative to each other in the state in which the slit nozzle is brought into contact with the surface of the mold 22, the surface of the mold 22 preferably has flatness.

A case where it is difficult for the polymer solution 200 to reach the corner of the recess of the recessed pattern 20A of the mold 22 due to the presence of the air is considered. Therefore, the supplying process is preferably performed under an environment at reduced pressure. The environment at reduced pressure means a state at or below atmospheric pressure. For example, by setting the mold 22 in a depressurization device (not illustrated) and supplying the polymer solution 200 to the mold 22, the polymer solution 200 can be supplied to the distal end of the recessed pattern 20A while the air is released from the recess under the environment at reduced pressure. This is particularly effective in a case where the mold 22 is a gas permeable material.

As another method, the mold 22 supplied with the polymer solution 200 is placed in a pressure vessel. After heating the inside of the pressure vessel to 40° C. using a heating jacket, compressed air is injected into the pressure vessel from a compressor. The air in the recess is removed by holding the inside of the pressure vessel at a pressure of 0.5 MPa for 5 minutes and applying a pressure to the mold, thereby enabling the polymer solution 200 to be supplied to the distal end of the recessed pattern 20A of the mold 22.

Figure 18C:
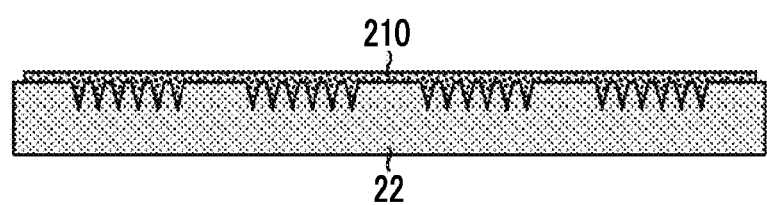
FIG. 18C is a diagram illustrating drying of the polymer solution in the process procedure of the manufacturing method of a pattern sheet using a mold.

FIG. 18C illustrates a drying process of drying the polymer solution 200 to form the polymer sheet 210. For example, the polymer solution 200 supplied to the mold 22 can be dried by blowing air thereto.

Drying is divided into, for example, four zones, and by setting conditions including (1) set dry at 15° C. (low humidity, wind speed 4 m/sec), (2) light wind drying at 35° C. (low humidity, wind speed 8 m/sec), (3) strong wind drying at 50° C. (wind speed 12 m/sec), and (4) strong wind drying at 30° C. (wind speed 20 m/sec), efficient drying can be performed.

The applied polymer solution 200 is dried, or the polymer solution 200 is gelated and then dried to solidify, thereby obtaining the polymer sheet 210. By gelating the polymer solution 200, the shape thereof can be reduced and a property of peeling the polymer solution 200 from the mold 22 can be enhanced. In this case, the polymer solution 200 can be gelated by flowing cold air at a low humidity. In order to completely gelate the polymer solution 200, cold air at 10 to 15 [° C.] is blown for a longer period of time than in the above case, and thereafter air is blown in the same manner as above. In addition, in this case, in a case where hot air at a high temperature is flowed for subsequent drying, if the temperature of hot air is too high, gelation of the polymer solution 200 is cancelled or the effect of the drug may change due to decomposition of the drug through heating. Therefore, the temperature of the blown air requires attention.

By forming the polymer sheet 210, the polymer sheet 210 is reduced in size compared to the state in a case where the polymer solution 200 is injected. Particularly, in a case where gelation is performed, the polymer sheet 210 is significantly reduced in size. Accordingly, peeling of the polymer sheet 210 from the mold 22 described later is facilitated.

The polymer sheet 210 means a state after a desired drying treatment is applied to the polymer solution 200. The moisture content of the polymer sheet 210 and the like are appropriately set.

Figure 18D:
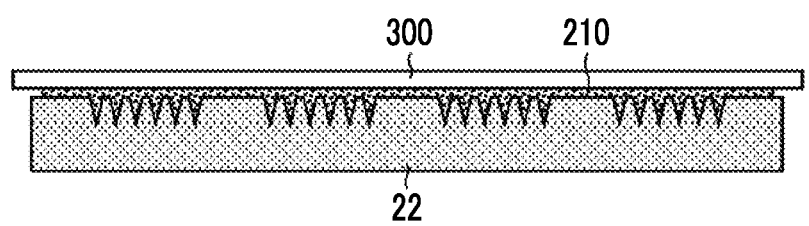
FIG. 18D is a diagram illustrating a polymer sheet before being peeled away from the mold in the process procedure of the manufacturing method of a pattern sheet using a mold.
Figure 18E:
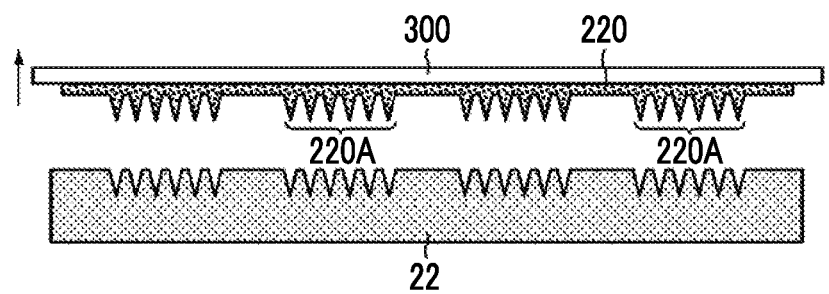
FIG. 18E is a diagram illustrating the polymer sheet after being peeled away from the mold in the process procedure of the manufacturing method of a pattern sheet using a mold.

FIGS. 18D and 18E illustrate a polymer sheet peeling process of peeling the polymer sheet 210 from the mold 22. As illustrated in FIG. 18D, a sheet-like base material 300 having a pressure sensitive adhesive layer formed thereon is attached to the surface of the polymer sheet 210 opposite to the mold 22. The surface of the base material 300 may be subjected to a surface activation treatment so as to be bonded. Furthermore, after the base material 300 is brought into close contact, the polymer solution may be applied thereto from above the base material 300 to bury the base material 300 therein. As a material of the sheet-like base material 300, for example, polyethylene terephthalate (PET), polypropylene (PP), polycarbonate (PC), or polyethylene (PE), may be used.

As illustrated in FIG. 18E, after the base material 300 is attached to the polymer sheet 210, the base material 300 and the polymer sheet 210 are simultaneously peeled away. A sucker (not illustrated) is placed on the surface of the base material 300 opposite to the bonding surface of the polymer sheet 210, and is pulled up vertically while sucking the base material 300 with air. The polymer sheet 210 is peeled away from the mold 22, thereby forming a pattern sheet 220 having a protruding pattern 220A.

It is preferable that the material forming the mold 22 is made of a material which can be very easily peeled away. Furthermore, by using a highly elastic and soft material as the material forming the mold 22, stress applied to the protruding pattern 220A of the pattern sheet 220 during peeling can be relieved.

The protruding pattern 220A of the pattern sheet 220 has the inverted shape of the recessed pattern 20A of the mold 22. Here, the pattern sheet 220 is basically the same as the polymer sheet 210 peeled away from the mold 22.

Figure 18F:
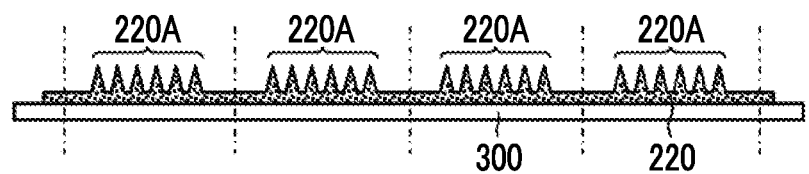
FIG. 18F is a diagram illustrating the polymer sheet before being cut into individual pattern sheets in the process procedure of the manufacturing method of a pattern sheet using a mold.
Figure 18G:
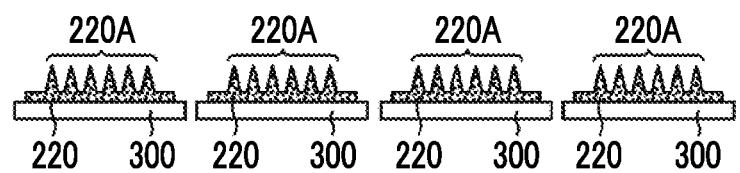
FIG. 18G is a diagram illustrating the polymer sheet after being cut into individual pattern sheets in the process procedure of the manufacturing method of a pattern sheet using a mold.

FIGS. 18F and 18G illustrate a cutting process of cutting the pattern sheet 220 into the individual pattern sheets 220.

As illustrated in FIG. 18F, the pattern sheet 220 having the protruding pattern 220A and the base material 300 peeled away from the mold 22 are set in a cutting device (not illustrated). The positions to cut the pattern sheet 220 are determined. Basically, the cutting position is determined for each protruding pattern 220A.

As illustrated in FIG. 18G, the pattern sheet 220 is cut into a plurality of the individual pattern sheets 220. In this embodiment, the example in which the pattern sheet 220 and the base material 300 are simultaneously cut is described, but the present invention is not limited thereto.

For example, the base material 300 may be peeled away from the pattern sheet 220 and the base material 300 peeled away from the mold 22, and the pattern sheet 220 may be cut into the individual pattern sheets 220.

In this embodiment, the case where the polymer sheet 210 is formed by filling the recessed pattern 20A with the polymer solution 200 and drying the polymer solution 200 is described, but the present invention is not limited thereto.

For example, a polymer sheet can be formed by filling the recessed pattern 20A with the polymer solution 200 containing the drug, drying the polymer solution 200, filling the recessed pattern 20A with the polymer solution 200 which does not contain a drug, and drying the polymer solution 200.

As long as the polymer solution 200 capable of forming the pattern sheet 220 is supplied, the number of times the polymer solution 200 is supplied and the presence or absence of the drug in the polymer solution 200 can be appropriately changed.

Figure 19:
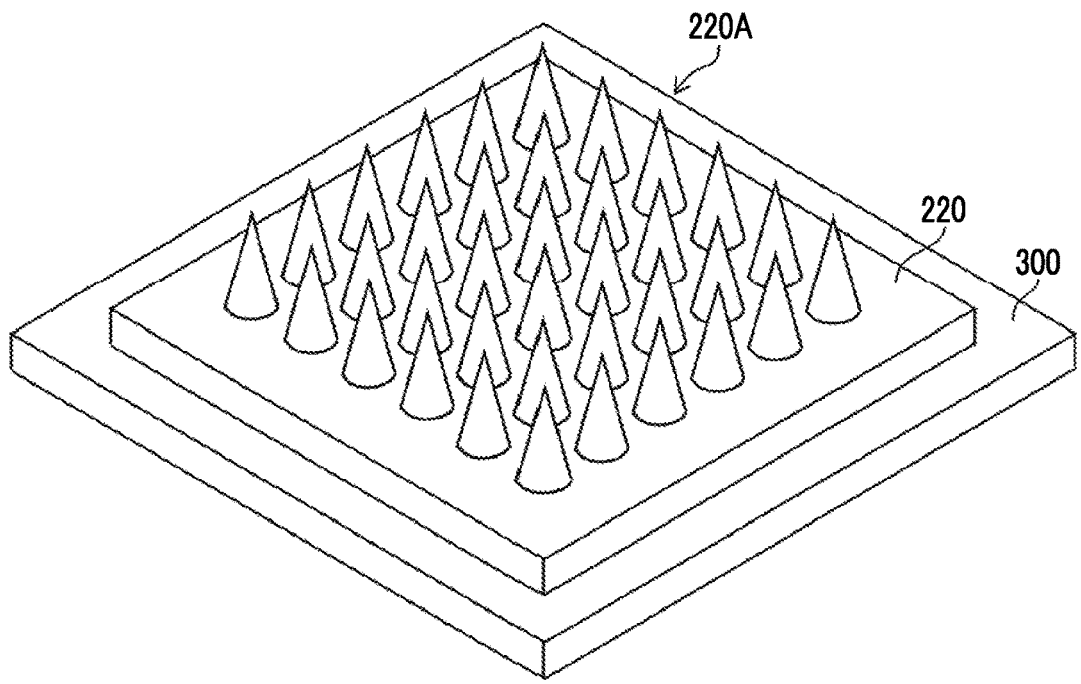
FIG. 19 is a perspective view of the individual pattern sheet.

FIG. 19 is a perspective view of the individual pattern sheet 220. The individual pattern sheet 220 has the protruding pattern 220A on one surface. In addition, the pattern sheet 220 has the base material 300 on the surface opposite to the surface on which the protruding pattern 220A is formed.

Figure 20A:
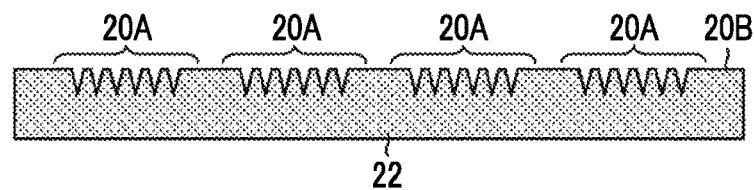
FIG. 20A is a diagram illustrating preparation of a mold in a process procedure of a production method of an electroform using a mold.
Figure 20B:
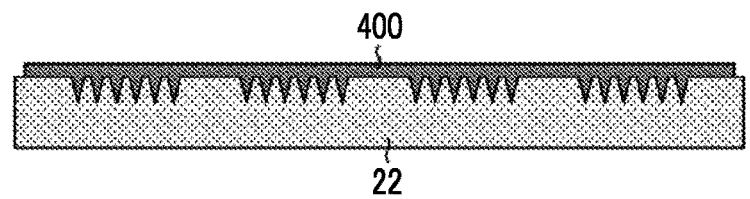
FIG. 20B is a diagram illustrating electroforming in the process procedure of the production method of an electroform using a mold.
Figure 20C:
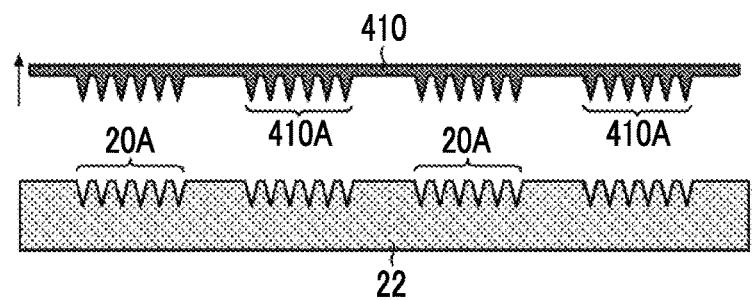
FIG. 20C is a diagram illustrating a metal body peeled away from the mold in the process procedure of the production method of an electroform using a mold.

Next, a method of producing an electroform using the mold 22 will be described. FIGS. 20A to 20C are process diagrams illustrating a procedure of the production method of an electroform using the mold 22.

FIG. 20A illustrates a state in which the mold 22 is prepared. The mold 22 is produced by the above-described production method of the mold 22, and the recessed pattern 20A is formed on the surface 20B of the mold 22.

FIG. 20B is a process diagram illustrating an electroforming process in which metal is buried in the recessed pattern 20A of the mold 22 by an electroforming method. In the electroforming process, first, a conduction treatment is performed on the mold 22. Metal (for example, nickel) is sputtered onto the mold 22 to deposit the metal on the surface of the mold 22 and the recessed pattern 20A.

Next, the mold 22 subjected to the conduction treatment is held at a cathode. Metal pellets are held in a metallic case as an anode. The cathode holding the mold 22 and the anode holding the metal pellets are immersed in an electroforming liquid to cause electricity to flow. The metal is buried in the recessed pattern 20A of the mold 22 by the electroforming method, thereby forming a metal body 400. The electroforming method refers to a method of depositing metal on the surface of a mold by an electroplating method.

FIG. 20C is a process diagram illustrating a peeling process of peeling the metal body 400 from the mold 22. As illustrated in FIG. 20C, the metal body 400 is peeled away from the mold 22, thereby producing an electroform 410 having a protruding pattern 410A. Peeling means the separation of the metal body 400 from the mold 22. The protruding pattern 410A has the inverted shape of the recessed pattern 20A of the mold 22. Here, the electroform 410 is basically the same as the metal body 400 peeled away from the mold 22.

In this embodiment, the mold 22 is produced using the plate precursor 10 illustrated in FIG. 2, and the electroform 410 is produced using the mold 22 illustrated in FIGS. 20A to 20C. Therefore, the electroform 410 having a larger area than the plate precursor 10 can be obtained. The electroform 410 has the same function as the plate precursor 10 in terms of being used as a plate precursor in a case where the mold 22 is produced, and has a larger area than the plate precursor 10. That is, since a plate precursor having a large area can be obtained by an electroforming method other than machining such as grinding, the costs for producing the plate precursor having a large area can be reduced.

Figure 21A:
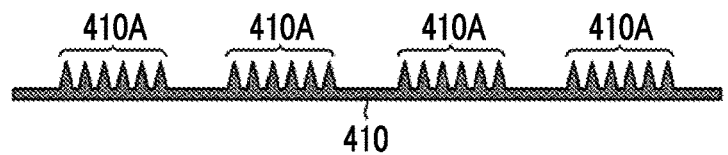
FIG. 21A is a diagram illustrating preparation of an electroform in a process procedure of a production method of a mold using an electroform.
Figure 21B:
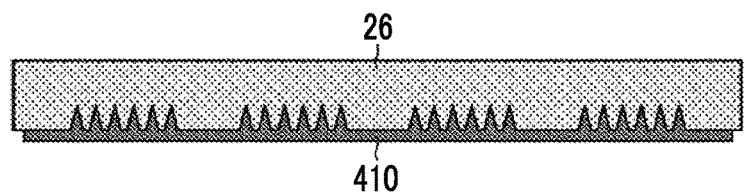
FIG. 21B is a diagram illustrating an ultraviolet curable resin which is pressed against the electroform in the process procedure of the production method of a mold using an electroform.
Figure 21C:
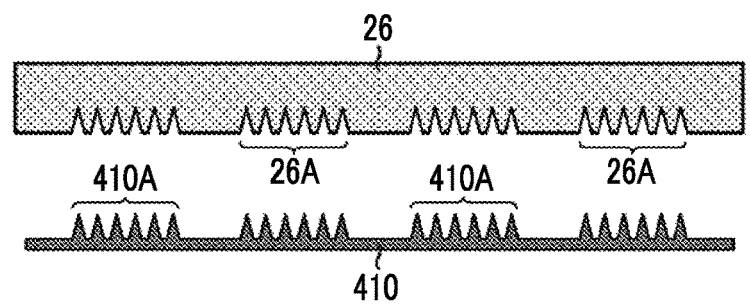
FIG. 21C is a diagram illustrating the electroform which is peeled away from the ultraviolet curable resin cured in the process procedure of the production method of a mold using an electroform.

Next, a method of producing a mold using the electroform 410 will be described. FIGS. 21A to 21C are process diagrams illustrating a procedure of the production method of the mold 26 using the electroform 410.

FIG. 21A illustrates a state in which the electroform 410 is prepared. The electroform 410 is produced by the above-described production method of the electroform 410. The electroform 410 has the protruding pattern 410A on one side.

FIGS. 21B and 21C are process diagrams illustrating a process of producing a mold 26 which has a recessed pattern 26A which has the inverted shape of the protruding pattern 410A of the electroform 410 and is made of a resin, by using the electroform 410 having the protruding pattern 410A. The recessed pattern 26A refers to a state in which recesses extending from one surface of the mold 26 toward the other surface are disposed on one surface of the mold 26. The number of recesses, the positions of the disposed recesses, and the like are not limited.

A method of producing the mold 26 using the electroform 410 will be described. The mold 26 having the recessed pattern 26A can be produced by the following first to third methods.

First, the first method will be described. An ultraviolet curable resin which is cured by being irradiated with ultraviolet rays is prepared. The protruding pattern 410A of the electroform 410 is pressed against the ultraviolet curable resin. In the state in which the electroform 410 is pressed against the ultraviolet curable resin, the ultraviolet curable resin is irradiated with ultraviolet rays such that the ultraviolet curable resin is cured. The electroform 410 is peeled away from the ultraviolet curable resin which is cured. The mold 26 having the recessed pattern 26A which has the inverted shape of the protruding pattern 410A of the electroform 410 and is made of the resin can be produced.

The second method will be described. A thermoplastic resin sheet as the material of the mold 26 is prepared. The electroform 410 having the protruding pattern 410A is heated. The protruding pattern 410A of the heated electroform 410 is pressed against the surface of the thermoplastic resin sheet. Since the surface of the thermoplastic resin is softened, the protruding pattern 410A is transferred onto the thermoplastic resin sheet.

In the state in which the electroform 410 is pressed against the thermoplastic resin sheet, the thermoplastic resin sheet and the electroform 410 are cooled. The thermoplastic resin sheet is cured by cooling the electroform 410. Thereafter, the electroform 410 is peeled away from the thermoplastic resin sheet to which the protruding pattern 410A has been transferred. The mold 26 having the recessed pattern 26A which has the inverted shape of the protruding pattern 410A of the electroform 410 and is made of the resin can be produced.

Next, the third method will be described. A silicone resin is prepared by adding a hardener to PDMS (polydimethylsiloxane, for example, SYLGARD 184 manufactured by Dow Corning Corporation. SYLGARD: trademark). The protruding pattern 410A of the electroform 410 is pressed against the silicone resin. In the state in which the electroform 410 is pressed against the silicone resin, the silicone resin is heated and cured at 100° C. The electroform 410 is peeled away from the cured silicone resin. The mold 26 having the recessed pattern 26A which has the inverted shape of the protruding pattern 410A of the electroform 410 and is made of the resin can be produced.

Since the recessed pattern 26A has the inverted shape of the protruding pattern 410A, the size of each recess of the recessed pattern 26A is substantially the same as the size of the protrusion of the protruding pattern 410A. However, the method of producing the mold 26 is not limited to the first to third methods.

Next, a manufacturing method of a pattern sheet having a protruding pattern using the mold 26 will be described. FIGS. 22A to 22G are process diagrams illustrating a procedure of the manufacturing method of the pattern sheet 220 using the mold 26. The process diagrams illustrating the procedure of the manufacturing method of the pattern sheet in FIGS. 18A to 18G and the process diagrams illustrating the procedure of the manufacturing method of the pattern sheet in FIGS. 224 to 22G are basically the same except for the difference between the mold 22 and the mold 26. Therefore, like configurations which are similar to those of the process diagrams illustrated in FIGS. 18A to 18G are denoted by like reference numerals, and the description thereof may be omitted in some cases.

Figure 22A:
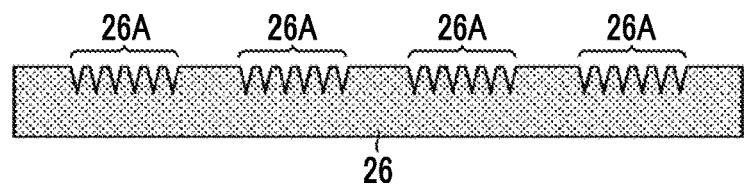
FIG. 22A is a diagram illustrating preparation of mold in a process procedure of a production method of a pattern sheet using a mold produced using an electroform.

FIG. 22A illustrates a state in which the mold 26 is prepared. As illustrated in FIGS. 21A to 21C described above, the mold 26 is produced using the electroform 410. The mold 26 has the recessed pattern 264 on one side.

Figure 22B:
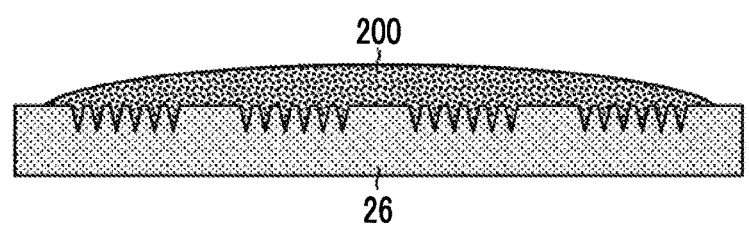
FIG. 22B is a diagram illustrating supply of a polymer solution to a recessed pattern in the process procedure of the production method of a pattern sheet using a mold produced using an electroform.

FIG. 22B illustrates a supplying process of supplying the polymer solution 200 to the recessed pattern 26A of the mold 26. The polymer solution 200 is basically the same as the polymer solution 200 described with reference to FIGS. 18A to 18G. As illustrated in FIG. 22B, the polymer solution 200 is supplied to the mold 26 such that the recessed pattern 264 is filled with the polymer solution 200. That is, the recesses constituting the recessed pattern 26A are filled with the polymer solution 200. As a method of filling the recesses of the recessed pattern 26A with the polymer solution 200, the filling methods described with reference to FIGS. 18A to 18G may be applied.

Figure 22C:
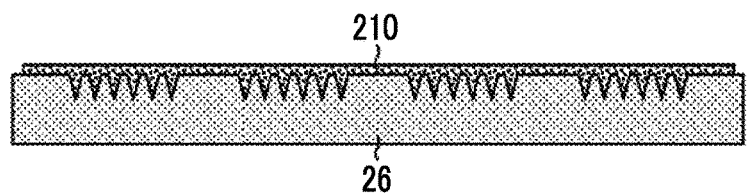
FIG. 22C is a diagram illustrating drying of the polymer solution in the process procedure of the production method of a pattern sheet using a mold produced using an electroform.

FIG. 22C illustrates a drying process of drying the polymer solution 200 to form the polymer sheet 210. For example, the polymer solution 200 supplied to the mold 26 can be dried by blowing air thereto. The drying method, conditions, and the like described with reference to FIGS. 18A to 18G can be applied.

Figure 22D:
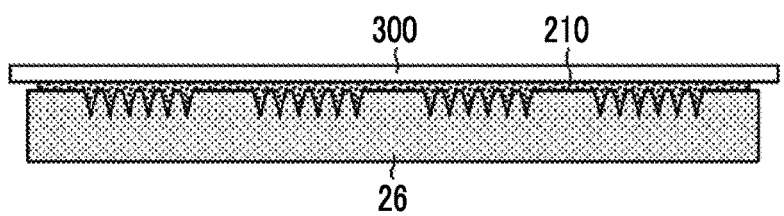
FIG. 22D is a diagram illustrating a polymer sheet before being peeled away from the mold in the process procedure of the production method of a pattern sheet using a mold produced using an electroform.
Figure 22E:
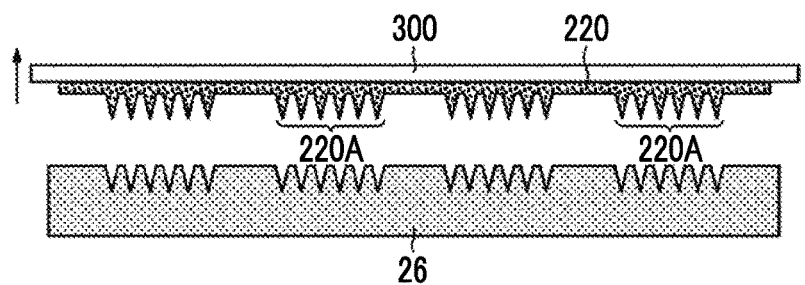
FIG. 22E is a diagram illustrating the polymer sheet after being peeled away from the mold in the process procedure of the production method of a pattern sheet using a mold produced using an electroform.

FIGS. 22D and 22E illustrate a polymer sheet peeling process of peeling the polymer sheet 210 from the mold 26. As illustrated in FIG. 22D, the sheet-like base material 300 having a pressure sensitive adhesive layer formed thereon is attached to the surface of the polymer sheet 210 opposite to the mold 26.

As illustrated in FIG. 22E, after the base material 300 is attached to the polymer sheet 210, the base material 300 and the polymer sheet 210 are simultaneously peeled away. A sucker (not illustrated) is placed on the surface of the base material 300 opposite to the bonding surface of the polymer sheet 210, and is pulled up vertically while sucking the base material 300 with air. The polymer sheet 210 is peeled away from the mold 26, thereby forming the pattern sheet 220 having the protruding pattern 220A.

It is more preferable that the material forming the mold 26 is made of a material which can be very easily peeled away. Furthermore, by using a highly elastic and soft material as the material forming the mold 26, stress applied to the protruding pattern 220A of the pattern sheet 220 during peeling can be relieved.

The protruding pattern 220A of the pattern sheet 220 has the inverted shape of the recessed pattern 26A of the mold 26. Here, the pattern sheet 220 is basically the same as the polymer sheet 210 peeled away from the mold 26.

Figure 22F:
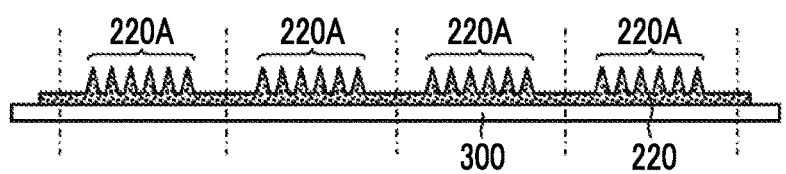
FIG. 22F is a diagram illustrating the polymer sheet before being cut into individual pattern sheets in the process procedure of the production method of a pattern sheet using a mold produced using an electroform.
Figure 22G:
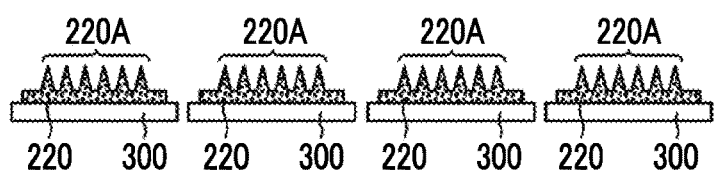
FIG. 22G is a diagram illustrating the polymer sheet after being cut into individual pattern sheets in the process procedure of the production method of a pattern sheet using a mold produced using an electroform.

FIGS. 22F and 22G illustrate a cutting process of cutting the pattern sheet 220 into the individual pattern sheets 220.

As illustrated in FIG. 22F, the pattern sheet 220 having the protruding pattern 220A and the base material 300 peeled away from the mold 26 are set in a cutting device (not illustrated). The positions to cut the pattern sheet 220 are determined. Basically, the cutting position is determined for each protruding pattern 220A.

As illustrated in FIG. 22G, the pattern sheet 220 is cut into a plurality of the individual pattern sheets 220. In this embodiment, the example in which the pattern sheet 220 and the base material 300 are simultaneously cut is described, but the present invention is not limited thereto.

For example, the base material 300 may be peeled away from the pattern sheet 220 and the base material 300 peeled away from the mold 26, and the pattern sheet 220 may be cut into the individual pattern sheets 220.

In this embodiment, the case where the polymer sheet 210 is formed by filling the recessed pattern 20A with the polymer solution 200 and drying the polymer solution 200 is described, but the present invention is not limited thereto.

For example, a polymer sheet can be formed by filling the recessed pattern 20A with the polymer solution 200 containing the drug, drying the polymer solution 200, filling the recessed pattern 20A with the polymer solution 200 which does not contain a drug, and drying the polymer solution 200.

As long as the polymer solution 200 capable of forming the pattern sheet 220 is supplied, the number of times the polymer solution 200 is supplied and the presence or absence of the drug in the polymer solution 200 can be appropriately changed.

As described above, according to this embodiment, the generation of a step between recessed patterns can be suppressed, the number of operations of producing the plate precursor can be reduced, and the productivity can be improved.

EXPLANATION OF REFERENCES

1: mold
2: step
3: duplicate mold
10: plate precursor
10A: protruding pattern
10B: flat surface
12: protrusion
12A: needle portion
12B: frustum portion
12C: columnar portion
20: thermoplastic resin sheet
20A: recessed pattern
20B: surface
22: mold
24: depression
24A: side surface
24B: bottom surface
26: mold
26A: recessed pattern
30: aligning apparatus
32: Z-axis drive mechanism
34: connection portion
36: holding portion
38: table
40: X-axis drive mechanism
42: Y-axis drive mechanism
44: stand
46: control system
48: laser displacement meter
200: polymer solution
210: polymer sheet
220: pattern sheet
220A: protruding pattern
300: base material
400: metal body
410: electroform
410A: protruding pattern
X: pressing surface
Y: outer surface
P: melted resin
Q: raised portion

What is claimed is:

1. A production method of a mold comprising:
   a preparation process of preparing a plate precursor having a protruding pattern formed of a plurality of protrusions in a pattern presence region on a base, and a thermoplastic resin sheet;
   an alignment process of determining a position at which the plate precursor is to be pressed against the thermoplastic resin sheet by moving the plate precursor and the thermoplastic resin sheet relative to each other; and
   a forming process of forming a recessed pattern having an inverted shape of the protruding pattern on the thermoplastic resin sheet by pressing the protrusions of the plate precursor which is heated against the thermoplastic resin sheet at a position where a part of the pattern presence region of the plate precursor excluding the protrusions is separated from a surface of the thermoplastic resin sheet, cooling the plate precursor in a state in which the pressed protrusions and the thermoplastic resin sheet are in contact with each other, and separating the plate precursor from the thermoplastic resin sheet,
   wherein a depression is formed in advance in a pressing surface in the surface of the thermoplastic resin sheet, against which the protrusions forming the protruding pattern of the plate precursor are pressed.

2. The production method of a mold according to claim 1, wherein a thickness of the thermoplastic resin sheet is equal to or greater than a height of the protrusions of the plate precursor.

3. The production method of a mold according to claim 1, wherein, in the forming process, in a case where a heating temperature of the plate precursor is equal to or lower than a melting point of the thermoplastic resin sheet, a vertical sectional shape of the depression is an arcuate shape.

4. The production method of a mold according to claim 1, wherein, in the forming process, in a case where a heating temperature of the plate precursor is equal to or higher than a melting point of the thermoplastic resin sheet, a vertical sectional shape of the depression is a rectangular shape.

5. The production method of a mold according to claim 1, wherein a pressing surface in the surface of the thermoplastic resin sheet, against which the protrusions forming the protruding pattern of the plate precursor are pressed, is flat, and
   in the forming process, the part of the pattern presence region of the plate precursor excluding the protrusions is stopped before reaching the flat pressing surface.

6. The production method of a mold according to claim 1, wherein, in a case where the plate precursor is pressed against the thermoplastic resin sheet, a position of the surface of the thermoplastic resin sheet is detected, and the plate precursor is pushed from the position of the surface of the thermoplastic resin sheet by a certain amount.

7. The production method of a mold according to claim 1, wherein, in a case where the plate precursor is pressed against the thermoplastic resin sheet, a pressure applied to the plate precursor is measured and is compared to a certain pressure value which is set, and the amount of the plate precursor being pushed is determined.

8. The production method of a mold according to claim 1, wherein the protrusion has a frustum portion and a needle portion which is tapered, in a direction away from the base of the plate precursor, and in the forming process, in a case where the plate precursor is pressed against the thermoplastic resin sheet, the frustum portion is brought into contact with the surface of the thermoplastic resin sheet.

9. A manufacturing method of a pattern sheet having a protruding pattern, comprising:

a process of producing a mold using the production method according to claim 1;

a supplying process of supplying a polymer solution to a recessed pattern of the mold;

a drying process of drying the polymer solution to form a polymer sheet; and a polymer sheet peeling process of peeling the polymer sheet from the mold.

10. A production method of an electroform having a protruding pattern, comprising:

a process of producing a mold using the production method according to claim 1;

an electroforming process of forming a metal body on a recessed pattern of the mold using an electroforming method; and a peeling process of peeling the metal body from the mold.

11. A production method of a mold using an electroform, comprising:

a process of producing an electroform using the production method according to claim 10; and a process of, by using the electroform having a protruding pattern, producing a mold which has a recessed pattern which is an inverted shape of the protruding pattern of the electroform and is made of a resin.

12. A manufacturing method of a pattern sheet having a protruding pattern, comprising:

a process of producing a mold, which is made of a resin, using the production method according to claim 11;

a supplying process of supplying a polymer solution to a recessed pattern of the mold;

a drying process of drying the polymer solution to form a polymer sheet; and a peeling process of peeling the polymer sheet from the mold made of a resin.

* * * * *